(12) United States Patent
Zhang et al.

(10) Patent No.: US 12,064,635 B2
(45) Date of Patent: *Aug. 20, 2024

(54) SUB-PERCEPTION CALIBRATION USING TIME DOMAIN SCALING

(71) Applicant: Boston Scientific Neuromodulation Corporation, Valencia, CA (US)

(72) Inventors: Tianhe Zhang, Studio City, CA (US); Changfang Zhu, Valencia, CA (US); Que T. Doan, West Hills, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 692 days.

This patent is subject to a terminal disclaimer.

(21) Appl. No.: 17/081,752

(22) Filed: Oct. 27, 2020

(65) Prior Publication Data
US 2021/0038898 A1    Feb. 11, 2021

Related U.S. Application Data

(63) Continuation of application No. 15/882,549, filed on Jan. 29, 2018, now Pat. No. 10,874,859.
(Continued)

(51) Int. Cl.
*A61N 1/36* (2006.01)
*A61N 1/05* (2006.01)
*A61N 1/372* (2006.01)

(52) U.S. Cl.
CPC ....... *A61N 1/36164* (2013.01); *A61N 1/0551* (2013.01); *A61N 1/36062* (2017.08);
(Continued)

(58) Field of Classification Search
CPC .... A61N 1/0551; A61N 1/055; A61N 1/0556; A61N 1/06; A61N 1/08; A61N 1/3603;
(Continued)

(56) References Cited

U.S. PATENT DOCUMENTS 8,380,301 B2    2/2013  Zhu
8,412,345 B2    4/2013  Moffitt
(Continued)

FOREIGN PATENT DOCUMENTS

EP    2508226 A1    10/2012
EP    3573702 B1    11/2022
(Continued)

OTHER PUBLICATIONS

Szlavik et al. "The effect of stimulus current pulse width on nerve fiber size recruitment patterns". Medical Engineering & Physics, vol. 21, Issues 6-7. 1999. pp. 507-515.*
(Continued)

*Primary Examiner* — Eugene T Wu
(74) *Attorney, Agent, or Firm* — Schwegman Lundberg & Woessner, P.A.

(57) ABSTRACT

An example of a system to program a neuromodulator to deliver neuromodulation to a neural target using a plurality of electrodes may comprise a programming control circuit configured to determine target energy allocations for the plurality of electrodes based on at least one target pole to provide a target sub-perception modulation field, and normalize the target sub-perception modulation field, including determine a time domain scaling factor to account for at least one property of a neural target or of a neuromodulation waveform, and apply the time domain scaling factor to the target energy allocations.

20 Claims, 23 Drawing Sheets

Related U.S. Application Data

(60) Provisional application No. 62/451,999, filed on Jan. 30, 2017.

(52) U.S. Cl.
CPC ..... *A61N 1/36071* (2013.01); *A61N 1/36132* (2013.01); *A61N 1/36139* (2013.01); *A61N 1/36185* (2013.01); *A61N 1/36189* (2013.01); *A61N 1/37247* (2013.01); *A61N 1/3615* (2013.01); *A61N 1/36171* (2013.01); *A61N 1/36175* (2013.01); *A61N 1/36178* (2013.01)

(58) Field of Classification Search
CPC ............ A61N 1/36031; A61N 1/36034; A61N 1/36062; A61N 1/36071; A61N 1/36128; A61N 1/36132; A61N 1/36135; A61N 1/36139; A61N 1/3614; A61N 1/36142; A61N 1/36146; A61N 1/3615; A61N 1/36153; A61N 1/36157; A61N 1/3616; A61N 1/36164; A61N 1/36167; A61N 1/36171; A61N 1/36175; A61N 1/36178; A61N 1/36182; A61N 1/36185; A61N 1/37241; A61B 5/04; A61B 5/04001; A61B 5/053; A61B 5/0538; A61B 5/06; A61B 5/061; A61B 5/063; A61B 5/065; A61B 5/068; A61B 5/40; A61B 5/4005; A61B 5/4029; A61B 5/4041; A61B 5/4047; A61B 5/4058; A61B 5/4064; A61B 5/407; A61B 5/4821; A61B 5/4824; A61B 5/4827; A61B 5/4887; A61B 5/4893; A61B 5/4896; A61B 5/6886

See application file for complete search history.

(56) References Cited

U.S. PATENT DOCUMENTS

| | | | |
|---|---|---|---|
| 8,909,350 | B2 | 12/2014 | Lee |
| 10,857,354 | B2 | 12/2020 | Zhang et al. |
| 10,874,859 | B2 | 12/2020 | Zhang et al. |
| 2004/0116978 | A1* | 6/2004 | Bradley ............ A61N 1/36071 607/48 |
| 2006/0195159 | A1 | 8/2006 | Bradley et al. |
| 2008/0215119 | A1 | 9/2008 | Woods et al. |
| 2009/0270947 | A1* | 10/2009 | Stone ............... A61N 1/0534 607/59 |
| 2010/0137944 | A1 | 6/2010 | Zhu |
| 2014/0236257 | A1 | 8/2014 | Parker et al. |
| 2014/0249599 | A1 | 9/2014 | Kaula et al. |
| 2015/0165202 | A1* | 6/2015 | Grandhe ............ A61N 1/36071 607/46 |
| 2015/0360031 | A1 | 12/2015 | Bornzin et al. |
| 2016/0082251 | A1 | 3/2016 | Moffitt et al. |
| 2016/0082252 | A1* | 3/2016 | Hershey ............ A61N 1/36071 607/46 |
| 2016/0082262 | A1 | 3/2016 | Parramon et al. |
| 2016/0082265 | A1 | 3/2016 | Moffitt et al. |
| 2016/0175594 | A1* | 6/2016 | Min .................... A61N 1/3615 607/62 |
| 2018/0110987 | A1 | 4/2018 | Parker |
| 2018/0214689 | A1 | 8/2018 | Zhang et al. |
| 2018/0214701 | A1 | 8/2018 | Zhang et al. |

FOREIGN PATENT DOCUMENTS

| | | |
|---|---|---|
| EP | 3573703 B1 | 12/2022 |
| WO | WO-2012088482 A1 | 6/2012 |
| WO | WO-2018140852 A1 | 8/2018 |

OTHER PUBLICATIONS

"U.S. Appl. No. 15/882,369, Non Final Office Action mailed Mar. 16, 2020", 13 pgs.

"U.S. Appl. No. 15/882,369, Notice of Allowance mailed Aug. 5, 2020", 5 pgs.

"U.S. Appl. No. 15/882,369, Response filed Jan. 6, 20 to Restriction Requirement mailed Nov. 4, 2019", 6 pgs.

"U.S. Appl. No. 15/882,369, Response filed Jun. 11, 20 to Non Final Office Action mailed Mar. 16, 2020", 12 pgs.

"U.S. Appl. No. 15/882,369, Restriction Requirement mailed Nov. 4, 2019", 5 pgs.

"U.S. Appl. No. 15/882,549, 312 Amendment filed Oct. 15, 2020", 6 pgs.

"U.S. Appl. No. 15/882,549, Non Final Office Action mailed Mar. 16, 2020", 11 pgs.

"U.S. Appl. No. 15/882,549, Notice of Allowance mailed Aug. 19, 2020", 7 pgs.

"U.S. Appl. No. 15/882,549, Response filed Jan. 6, 20 to Restriction Requirement mailed Nov. 4, 2019", 6 pgs.

"U.S. Appl. No. 15/882,549, Response filed Jun. 11, 2020 to Non Final Office Action mailed Mar. 16, 2020", 12 pgs.

"U.S. Appl. No. 15/882,549, Restriction Requirement mailed Nov. 4, 2019", 6 pgs.

"European Application Serial No. 18705234.5, Response to Communication Pursuant to Rules 161 and 162 filed Mar. 18, 2020", 5 pgs.

"European Application Serial No. 18713420.0, Response to Communication Pursuant to Rules 161 and 162 filed Mar. 17, 2020", 5 pgs.

"International Application Serial No. PCT/US2018/015681, International Preliminary Report on Patentability mailed Aug. 8, 2019", 8 pgs.

"International Application Serial No. PCT/US2018/015681, International Search Report mailed Jun. 25, 2018", 4 pgs.

"International Application Serial No. PCT/US2018/015681, Written Opinion mailed Jun. 25, 2018", 8 pgs.

"International Application Serial No. PCT/US2018/015706, International Preliminary Report on Patentability mailed Aug. 8, 2019", 8 pgs.

"International Application Serial No. PCT/US2018/015706, International Search Report mailed Apr. 17, 2018", 4 pgs.

"International Application Serial No. PCT/US2018/015706, Written Opinion mailed Apr. 17, 2018", 6 pgs.

Szlavik, et al., "The effect of stimulus current pulse width on nerve fiber size recruitment patterns", Medical Engineering & Physics, vol. 21, Issues 6-7, 507-515.

"U.S. Appl. No. 15/882,549, PTO Response to Rule 312 Communication mailed Nov. 18, 2020", 2 pgs.

* cited by examiner

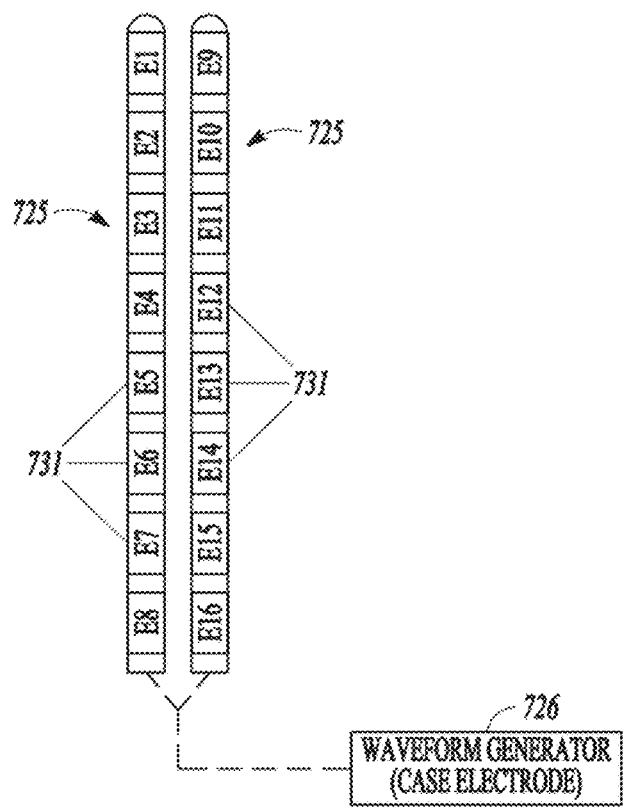
FIG. 7
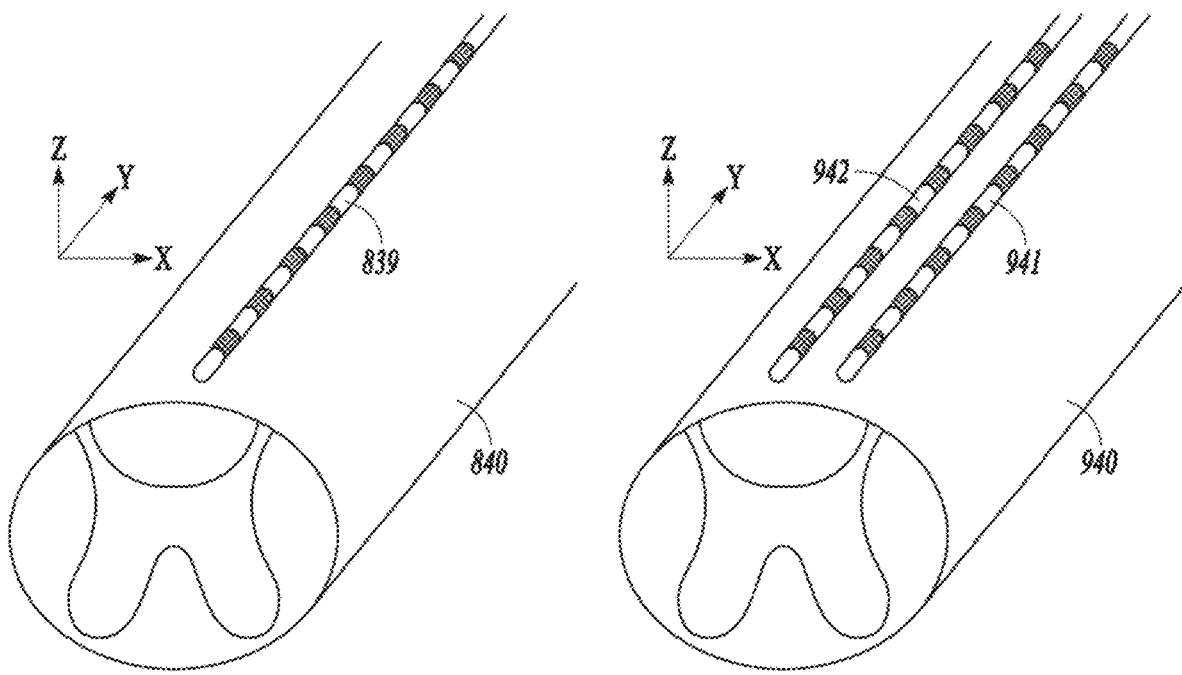
FIG. 8     FIG. 9

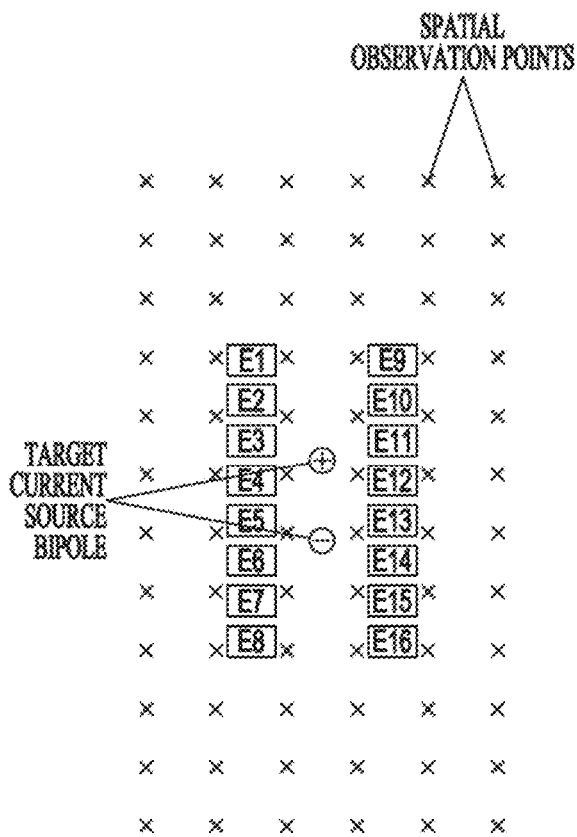 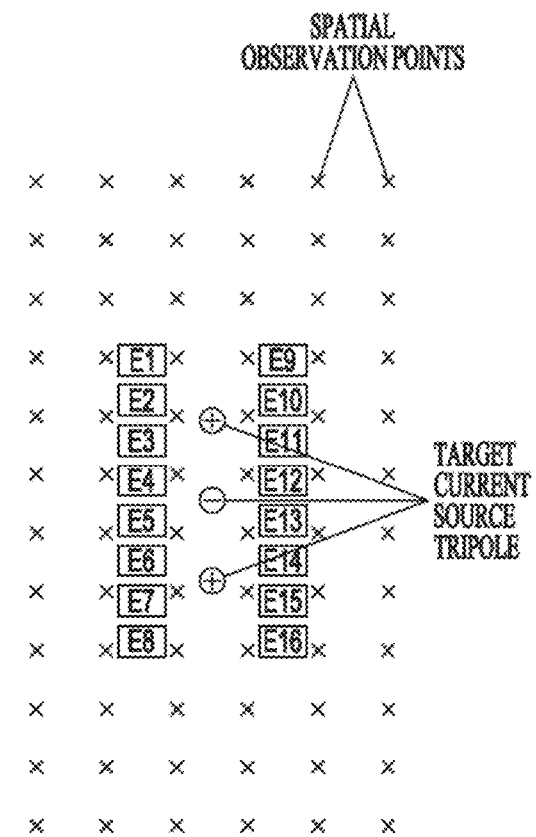
*FIG. 18A*  *FIG. 18B*
*FIG. 19A*  *FIG. 19B*  *FIG. 19C*

TRANSFER MATRIX A $(m \times n)$ $\begin{bmatrix} \text{m field potential values due to constituent source \#1} & \text{m field potential values due to constituent source \#2} & \text{m field potential values due to constituent source \#3} & \cdots & \text{m field potential values due to constituent source \#n} \end{bmatrix}$

*FIG. 20*

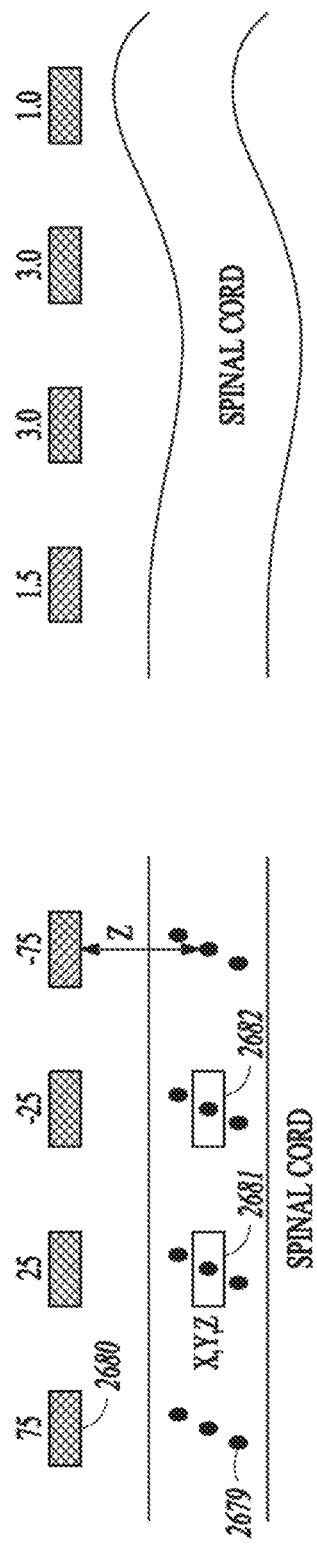
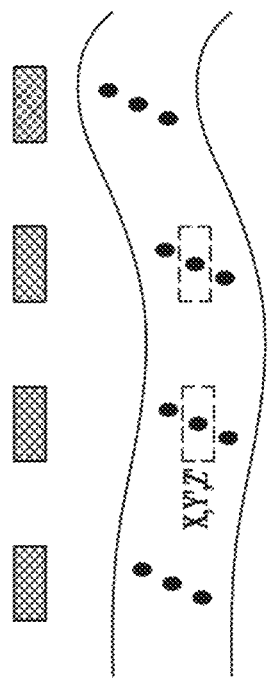
FIG. 26A
FIG. 26B
FIG. 26C

SUB-PERCEPTION CALIBRATION USING TIME DOMAIN SCALING

CLAIM OF PRIORITY

This application is a continuation of U.S. application Ser. No. 15/882,549, filed Jan. 29, 2018, which claims the benefit of priority under 35 U.S.C. § 119(e) of U.S. Provisional Patent Application Ser. No. 62/451,999, filed on Jan. 30, 2017, each of which is herein incorporated by reference in its entirety.

CROSS REFERENCE TO RELATED APPLICATION

This application is related to commonly assigned U.S. Provisional Patent Application Ser. No. 62/451,994, entitled "SUB-PERCEPTION CALIBRATION USING SPACE DOMAIN SCALING", filed on Jan. 30, 2017, which is incorporated by reference in its entirety.

TECHNICAL FIELD

This document relates generally to medical devices, and more particularly, but not by way of limitation, to systems, devices, and methods to provide a neuromodulation field.

BACKGROUND

Neural modulation has been proposed as a therapy for a number of conditions. Often, neural modulation and neural stimulation may be used interchangeably to describe excitatory stimulation that causes action potentials as well as inhibitory and other effects. Examples of neuromodulation include Spinal Cord Stimulation (SCS), Deep Brain Stimulation (DBS), Peripheral Nerve Stimulation (PNS), and Functional Electrical Stimulation (FES). SCS, by way of example and not limitation, has been used to treat chronic pain syndromes. Some neural targets may be complex structures with different types of nerve fibers. An example of such a complex structure is the neuronal elements in and around the spinal cord targeted by SCS.

Neuromodulation energy may be delivered to provide sub-perception modulation that is therapeutically effective, but the delivery of the sub-perception modulation energy is not perceivable by the patient. Since the patient does not perceive the delivery of sub-perception energy, it can be difficult to accurately program a target sub-perception field as patient feedback is not available for real-time adjustments to the modulation.

SUMMARY

This document discusses, among other things, systems and methods to define electrode parameters for neuromodulation such as sub-perception SCS. The present inventors have recognized, among other things, that real clinical outcomes depend on patient-to-patient differences in electrode-tissue coupling and neural excitability and that the allocation of energy to the electrodes for the target pole can be improved using space domain scaling to compensate for patient-specific displacement between electrodes or between electrode and tissue, and/or using time domain scaling to account for at least one property of a neural target or of a neuromodulation waveform.

An example (e.g. "Example 1") of a non-transient machine readable medium may contain program instructions for causing a machine to: determine target electrode fractionalization contributions energy allocations for a plurality of electrodes based on at least one target pole to provide a target sub-perception modulation field; and normalize the target sub-perception modulation field, including determining a time domain scaling factor to account for at least one property of a neural target or of a neuromodulation waveform, and applying the time domain scaling factor to the target energy allocations.

In Example 2, the subject matter of Example 1 may optionally be configured such that the determine the time domain scaling factor includes determine the time domain scaling factor based on a type of neural structure.

In Example 3, the subject matter of any one or any combination of Examples 1-2 may optionally be configured such that the determine the time domain scaling factor includes determine the time domain scaling factor based on at least one neural structure property, the at least one neural structure property including a geometrical property or an electrical property.

In Example 4, the subject matter of any one or any combination of Examples 1-3 may optionally be configured such that the determine the time domain scaling factor includes determine the time domain scaling factor based on a pulse width of the neuromodulation waveform.

In Example 5, the subject matter of any one or any combination of Examples 1-4 may optionally be configured such that the determine the time domain scaling factor includes determine the time domain scaling factor based on a frequency of the neuromodulation waveform.

In Example 6, the subject matter of any one or any combination of Examples 1-5 may optionally be configured such that the determine the time domain scaling factor includes determine the time domain scaling factor based on a duty cycle of the neuromodulation waveform.

In Example 7, the subject matter of any one or any combination of Examples 1-6 may optionally be configured such that the determine the time domain scaling factor includes determine the time domain scaling factor based on a shape or pattern of the neuromodulation waveform.

In Example 8, the subject matter of any one or any combination of Examples 1-7 may optionally be configured such that the determine the time domain scaling factor includes determine the time domain scaling factor based on a type of the neuromodulation waveform.

In Example 9, the subject matter of any one or any combination of Examples 1-8 may optionally be configured such that the normalize the target sub-perception modulation field includes determine the time domain scaling factor to account for at least one property of the neural target and for at least one property of the neuromodulation waveform.

In Example 10, the subject matter of any one or any combination of Examples 1-9 may optionally be configured such that the normalize the target sub-perception modulation field includes determine the time domain scaling factor to account for at a first property and a second property selected from the group consisting of: a type of neural structure; at least one neural structure property, the at least one neural structure property including a geometrical property or an electrical property; and a neuromodulation waveform property. The waveform property may include a pulse width of the neuromodulation waveform; a frequency of the neuromodulation waveform; a duty cycle of the neuromodulation waveform; a shape or pattern of the neuromodulation waveform; and a type of the neuromodulation waveform.

In Example 11, the subject matter of Example 10 may optionally be configured such that the determine the time domain scaling factor to account for at the first property and the second property includes determine a first time domain scaling factor to account for the first property, determine a second time domain scaling factor to account for the second property, and multiplying the first time domain scaling factor and the second time domain scaling factor.

In Example 12, the subject matter of any one or any combination of Examples 1-11 may optionally further comprise program instructions for causing the machine to calibrate a plurality of electrode groups in the plurality of electrodes where each of the plurality of electrode groups have an electrode configuration and include an electrode set of at least one electrode from the plurality of electrodes, wherein the calibrating the electrode groups includes, for each of the plurality of electrode groups, delivering modulation energy to a neural target and receiving feedback, and determining a space scaling factor using the feedback to account for actual relative positions between the electrode groups and the neural target, and further applying the space domain scaling factor to the target energy allocations.

In Example 13, the subject matter of any one or any combination of Examples 1-12 may optionally be configured such that the determining the time domain scaling factor includes retrieve the time domain scaling factor from a lookup table or calculate the time domain scaling factor from a modeled analytic relationship.

An example (e.g. "Example 14") of a method may comprise determining target energy allocations for a plurality of electrodes based on at least one target pole to provide a target sub-perception modulation field, and normalizing the target sub-perception modulation field, including determining a time domain scaling factor to account for at least one property of a neural target or of a neuromodulation waveform, and applying the time domain scaling factor to the target energy allocations.

In Example 15, the subject matter of Example 14 may optionally be configured such that the determining the time domain scaling factor includes determining the time domain scaling factor based on a type of neural structure.

In Example 16, the subject matter of any one or any combination of Examples 14-15 may optionally be configured such that the determining the time domain scaling factor includes determining the time domain scaling factor based on at least one neural structure property, the at least one neural structure property including a geometrical property or an electrical property.

In Example 17, the subject matter of any one or any combination of Examples 14-16 may optionally be configured such that the determining the time domain scaling factor includes determining the time domain scaling factor based on a pulse width of the neuromodulation waveform.

In Example 18, the subject matter of any one or any combination of Examples 14-17 may optionally be configured such that the determining the time domain scaling factor includes determining the time domain scaling factor based on a frequency of the neuromodulation waveform.

In Example 19, the subject matter of any one or any combination of Examples 14-18 may optionally be configured such that the determining the time domain scaling factor includes determining the time domain scaling factor based on a duty cycle of the neuromodulation waveform.

In Example 20, the subject matter of any one or any combination of Examples 14-19 may optionally be configured such that the determining the time domain scaling factor includes determining the time domain scaling factor based on a shape or pattern of the neuromodulation waveform.

In Example 21, the subject matter of any one or any combination of Examples 14-20 may optionally be configured such that the determining the time domain scaling factor includes determining the time domain scaling factor based on a type of the neuromodulation waveform.

In Example 22, the subject matter of any one or any combination of Examples 14-21 may optionally be configured such that the normalizing the target sub-perception modulation field includes determining the time domain scaling factor to account for at least one property of the neural target and for at least one property of the neuromodulation waveform.

In Example 23, the subject matter of any one or any combination of Examples 14-22 may optionally be configured such that the normalizing the target sub-perception modulation field includes determining the time domain scaling factor to account for at a first property and a second property selected from the group consisting of: a type of neural structure; at least one neural structure property, the at least one neural structure property including a geometrical property or an electrical property; and a neuromodulation waveform property. The neuromodulation waveform property may include a pulse width of the neuromodulation waveform; a frequency of the neuromodulation waveform; a duty cycle of the neuromodulation waveform; a shape or pattern of the neuromodulation waveform; and a type of the neuromodulation waveform.

In Example 24, the subject matter of Example 23 may optionally be configured such that the determining the time domain scaling factor to account for at the first property and the second property includes determining a first time domain scaling factor to account for the first property, determining a second time domain scaling factor to account for the second property, and multiplying the first time domain scaling factor and the second time domain scaling factor.

In Example 25, the subject matter of any one or any combination of Examples 14-24 may optionally be configured such that the method may further comprise calibrating a plurality of electrode groups in the plurality of electrodes where each of the plurality of electrode groups have an electrode configuration and include an electrode set of at least one electrode from the plurality of electrodes, wherein the calibrating the electrode groups includes, for each of the plurality of electrode groups, delivering modulation energy to a neural target and receiving feedback, and determining a space scaling factor using the feedback to account for actual relative positions between the electrode groups and the neural target, and further applying the space domain scaling factor to the target energy allocations.

In Example 26, the subject matter of any one or any combination of Examples 14-25 may optionally be configured such that the determining the time domain scaling factor includes retrieving the time domain scaling factor from a lookup table.

In Example 27, the subject matter of any one or any combination of Examples 14-26 may optionally be configured such that the determining the time domain scaling factor includes calculating the time domain scaling factor from a modeled analytic relationship between a threshold of the neural target and the at least one property of the neural target or of the neuromodulation waveform.

An example (e.g. "Example 28") of a system to program a neuromodulator to deliver neuromodulation to a neural target using a plurality of electrodes may comprise a programming control circuit configured to determine target energy allocations for the plurality of electrodes based on at least one target pole to provide a target sub-perception modulation field, and normalize the target sub-perception modulation field, including determine a time domain scaling factor to account for at least one property of a neural target or of a neuromodulation waveform, and apply the time domain scaling factor to the target energy allocations.

In Example 29, the subject matter of Example 28 may optionally be configured such that system may further comprise an external device that includes the programming control circuit and a user interface, wherein the external device is configured to program parameter sets into an implantable modulation device.

In Example 30, the subject matter of any one or any combination of Examples 14-26 may optionally be configured such that the programming control circuit is configured to determine the time domain scaling factor to account for at least one property of the neural target and to account for at least one property of the neuromodulation waveform.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 7 illustrates, by way of example, some features of the neuromodulation leads and a waveform generator.

FIG. 8 is a schematic view of a single electrical modulation lead implanted over approximately the longitudinal midline of the patient's spinal cord.

FIG. 9 illustrates an embodiment where an electrical modulation lead has been implanted more laterally with respect to the spinal cord, thereby placing it proximate the dorsal horn of the spinal cord, and the other electrical modulation lead has been implanted more medially with respect to the spinal cord, thereby placing it proximate the dorsal column of the spinal cord.

FIGS. 18A-18B illustrate, by way of example, mapping a target electrical field to an electrode array.

FIGS. 19A-19C, illustrate, by way of example, selection of a plurality of constituent current sources at the locations of the electrodes.

FIG. 20 illustrates an m×n transfer matrix used to determine the relative strengths of constituent current sources.

FIG. 26A illustrates a calculated target field in the ideal environment;

FIG. 26B illustrates a real spinal cord environment; and FIG. 26C illustrates the moved observation points of the real spinal cord environment.

DETAILED DESCRIPTION

Target poles have been used to define electrode parameters for spinal cord stimulation (SCS) such as sub-perception SCS. The present inventors have recognized, among other things, that the allocation of energy to the electrodes for the target pole can be improved using space domain scaling to compensate for patient-specific displacement between electrodes or between electrode and tissue, and/or using time domain scaling to account for at least one property of a neural target or of a neuromodulation waveform.

Figure 1:
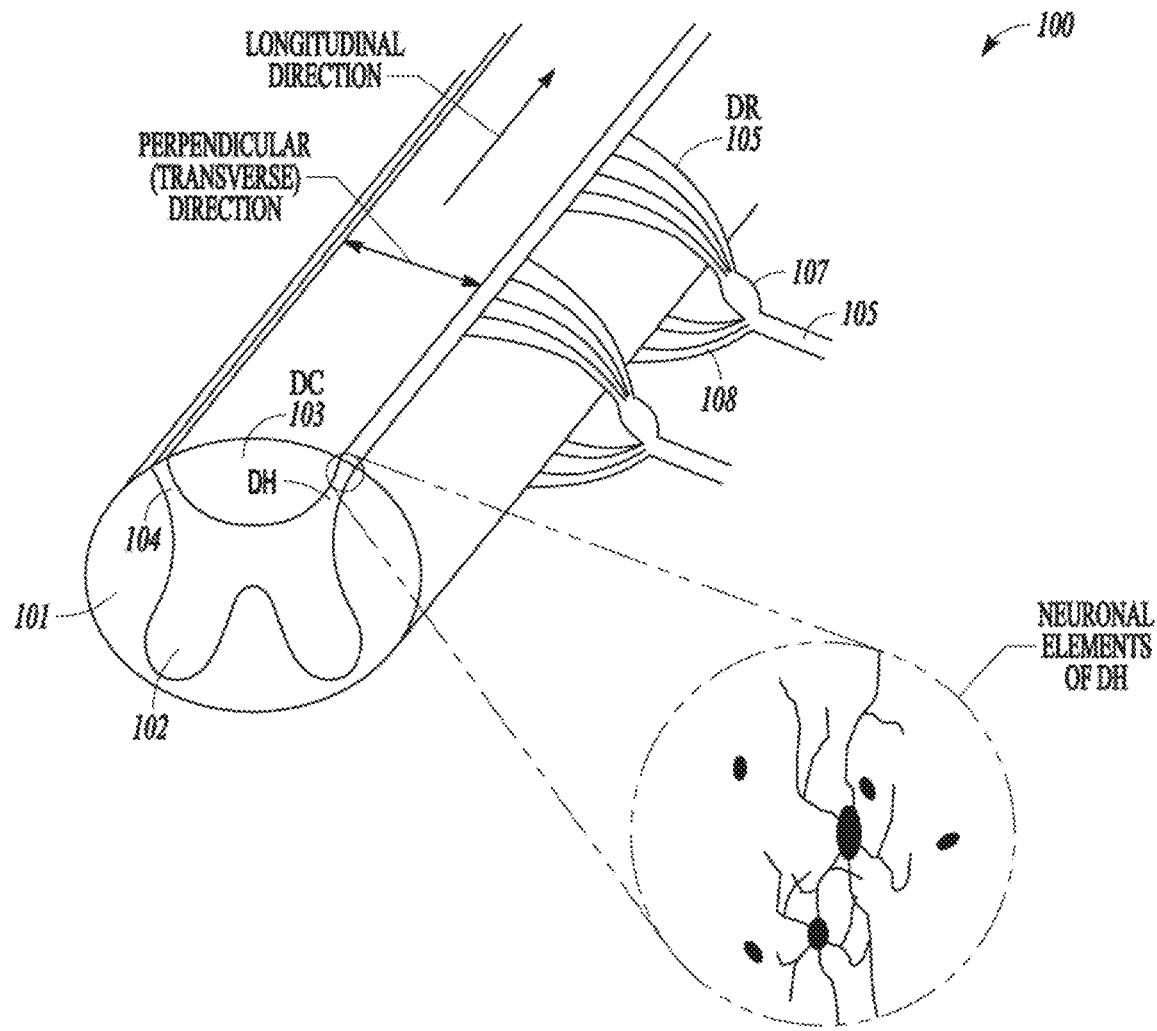
FIG. 1 illustrates, by way of example, a portion of a spinal cord.

Various embodiments described herein involve spinal cord modulation. A brief description of the physiology of the spinal cord is provided herein to assist the reader. FIG. 1 illustrates, by way of example, a portion of a spinal cord 100 including white matter 101 and gray matter 102 of the spinal cord. The gray matter 102 includes cell bodies, synapse, dendrites, and axon terminals. White matter 101 includes myelinated axons that connect gray matter areas. A typical transverse section of the spinal cord includes a central "butterfly" shaped central area of gray matter 102 substantially surrounded by an ellipse-shaped outer area of white matter 101. The white matter of the dorsal column (DC) 103 includes mostly large myelinated axons that form afferent fibers that run in an axial direction. The dorsal portions of the "butterfly" shaped central area of gray matter are referred to as dorsal horns (DH) 104. In contrast to the DC fibers that run in an axial direction, DH fibers can be oriented in many directions, including perpendicular to the longitudinal axis of the spinal cord. Examples of spinal nerves 105 are also illustrated, including a dorsal root (DR) 105, dorsal root ganglion 107 and ventral root 108. The dorsal root 105 mostly carries sensory signals into the spinal cord, and the ventral root functions as an efferent motor root. The dorsal and ventral roots join to form mixed spinal nerves 105.

SCS has been used to alleviate pain. A therapeutic goal for conventional SCS programming has been to maximize stimulation (i.e., recruitment) of the DC fibers that run in the white matter along the longitudinal axis of the spinal cord and minimal stimulation of other fibers that run perpendicular to the longitudinal axis of the spinal cord (dorsal root fibers, predominantly), as illustrated in FIG. 1. The white matter of the DC includes mostly large myelinated axons that form afferent fibers. While the full mechanisms of pain relief are not well understood, it is believed that the perception of pain signals is inhibited via the gate control theory of pain, which suggests that enhanced activity of innocuous touch or pressure afferents via electrical stimulation creates interneuronal activity within the DH of the spinal cord that releases inhibitory neurotransmitters (Gamma-Aminobutyric Acid (GABA), glycine), which in turn, reduces the hypersensitivity of wide dynamic range (WDR) sensory neurons to noxious afferent input of pain signals traveling from the dorsal root (DR) neural fibers that innervate the pain region of the patient, as well as treating general WDR ectopy. Consequently, the large sensory afferents of the DC nerve fibers have been conventionally targeted for stimulation at an amplitude that provides pain relief. Current implantable neuromodulation systems typically include electrodes implanted adjacent, i.e., resting near, or upon the dura, to the dorsal column of the spinal cord of the patient and along a longitudinal axis of the spinal cord of the patient.

Activation of large sensory DC nerve fibers also typically creates the paresthesia sensation that often accompanies conventional SCS therapy. Although alternative or artifactual sensations, such as paresthesia, are usually tolerated relative to the sensation of pain, patients sometimes report these sensations to be uncomfortable, and therefore, they can be considered an adverse side-effect to neuromodulation therapy in some cases. Some embodiments deliver sub-perception therapy that is therapeutically effective to treat pain, for example, but the patient does not sense the delivery of the modulation field (e.g. paresthesia). Sub-perception therapy may include higher frequency modulation (e.g. about 1000 Hz or above) of the spinal cord that effectively blocks the transmission of pain signals in the afferent fibers in the DC. Some embodiments may implement this higher frequency modulation may include 1200 Hz or above, and some embodiments may implement this higher frequency modulation may include 1500 Hz or above. Some embodiments herein selectively modulate DH tissue, such as the presynaptic terminals of pain inhibitory neurons in the spinal cord, over DC tissue. Some embodiments selectively stimulate DR tissue and/or dorsal root ganglion over DC tissue to provide sub-perception therapy. As will be described in further detail below, some embodiments described herein target axons from inhibitory interneurons that propagate in anterior-posterior direction aligned with an electric field. Certain myelinated presynaptic terminals of inhibitory neurons oriented in the anterior-posterior (AP) direction, i.e. in parallel with electric field, may polarize more than their unmyelinated, differently oriented counterparts. Polarization may produce both subthreshold and suprathreshold effects that result in positive clinical effects, and sub-threshold progressive effects may also explain clinical observations of wash-in and wash-out effects. The terminal appears to may be the point of the greatest polarization. The unmyelinated dendrites to not polarize as much.

Such selective modulation is not delivered at these higher frequencies. For example, the selective modulation may be delivered at frequencies less than 1,200 Hz. The selective modulation may be delivered at frequencies less than 1,000 Hz in some embodiments. In some embodiments, the selective modulation may be delivered at frequencies less than 500 Hz. In some embodiments, the selective modulation may be delivered at frequencies less than 350 Hz. In some embodiments, the selective modulation may be delivered at frequencies less than 130 Hz. The selective modulation may be delivered at low frequencies (e.g. as low as 2 Hz). The selective modulation may be delivered even without pulses (e.g. 0 Hz) to modulate some neural tissue. By way of example and not limitation, the selective modulation may be delivered within a frequency range selected from the following frequency ranges: 2 Hz to 1,200 Hz; 2 Hz to 1,000 Hz, 2 Hz to 500 Hz; 2 Hz to 350 Hz; or 2 Hz to 130 Hz. Systems may be developed to raise the lower end of any these ranges from 2 Hz to other frequencies such as, by way of example and not limitation, 10 Hz, 20 Hz, 50 Hz or 100 Hz. By way of example and not limitation, it is further noted that the selective modulation may be delivered with a duty cycle, in which stimulation (e.g. a train of pulses) is delivered during a Stimulation ON portion of the duty cycle, and is not delivered during a Stimulation OFF portion of the duty cycle. By way of example and not limitation, the duty cycle may be about 10%±5%, 20%±5%, 30%±5%, 40%±5%, 50%±5% or 60%±5%. For example, a burst of pulses for 10 ms during a Stimulation ON portion followed by 15 ms without pulses corresponds to a 40% duty cycle. The selected modulation may be delivered with fixed widths. Although the target field can be applied to any pulse width that the device is capable of delivering, longer pulses widths are believed to be more effective.

Figure 2:
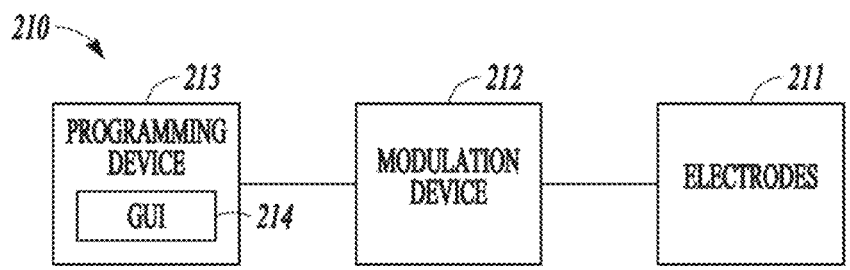
FIG. 2 illustrates, by way of example, an embodiment of a neuromodulation system.

FIG. 2 illustrates, by way of example, an embodiment of a neuromodulation system. The illustrated system 210 includes electrodes 211, a modulation device 212, and a programming system such as a programming device 213. The programming system may include multiple devices. The electrodes 211 are configured to be placed on or near one or more neural targets in a patient. The modulation device 212 is configured to be electrically connected to electrodes 211 and deliver neuromodulation energy, such as in the form of electrical pulses, to the one or more neural targets though electrodes 211. The delivery of the neuromodulation is controlled by using a plurality of modulation parameters. The modulation parameters may specify the electrical waveform (e.g. pulses or pulse patterns or other waveform shapes) and a selection of electrodes through which the electrical waveform is delivered. In various embodiments, at least some parameters of the plurality of modulation parameters are programmable by a user, such as a physician or other caregiver. The programming device 213 provides the user with accessibility to the user-programmable parameters. In various embodiments, the programming device 213 is configured to be communicatively coupled to modulation device via a wired or wireless link. In various embodiments, the programming device 213 includes a graphical user interface (GUI) 214 that allows the user to set and/or adjust values of the user-programmable modulation parameters.

Figure 3:
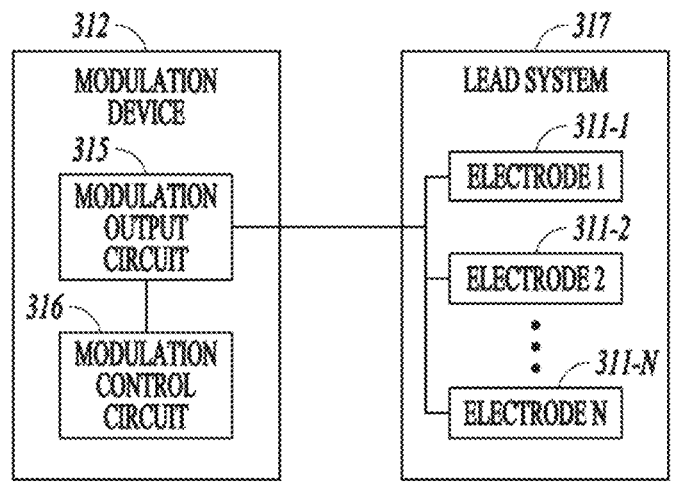
FIG. 3 illustrates, by way of example, an embodiment of a modulation device, such as may be implemented in the neuromodulation system of FIG. 2.

FIG. 3 illustrates an embodiment of a modulation device 312, such as may be implemented in the neuromodulation system 210 of FIG. 2. The illustrated embodiment of the modulation device 312 includes a modulation output circuit 315 and a modulation control circuit 316. Those of ordinary skill in the art will understand that the neuromodulation system 210 may include additional components such as sensing circuitry for patient monitoring and/or feedback control of the therapy, telemetry circuitry and power. The modulation output circuit 315 produces and delivers the neuromodulation. Neuromodulation pulses are provided herein as an example. However, the present subject matter is not limited to pulses, but may include other electrical waveforms (e.g. waveforms with different waveform shapes, and waveforms with various pulse patterns). The modulation control circuit 316 controls the delivery of the neuromodulation pulses using the plurality of modulation parameters. The lead system 317 includes one or more leads each configured to be electrically connected to modulation device 312 and a plurality of electrodes 311-1 to 311-N, where N≥2, distributed in an electrode arrangement using the one or more leads. Each lead may have an electrode array consisting of two or more electrodes, which also may be referred to as contacts. Multiple leads may provide multiple electrode arrays to provide the electrode arrangement. Each electrode is a single electrically conductive contact providing for an electrical interface between modulation output circuit 315 and tissue of the patient. The neuromodulation pulses are each delivered from the modulation output circuit 315 through a set of electrodes selected from the electrodes 311-1 to 311-N. The number of leads and the number of electrodes on each lead may depend on, for example, the distribution of target(s) of the neuromodulation and the need for controlling the distribution of electric field at each target. In one embodiment, by way of example and not limitation, the lead system includes two leads each having eight electrodes. Some embodiments may use a lead system that includes a paddle lead.

The neuromodulation system may be configured to modulate spinal target tissue or other neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. An electrical waveform may be controlled or varied for delivery using electrode configuration(s). The electrical waveforms may be analog or digital signals. In some embodiments, the electrical waveform includes pulses. The pulses may be delivered in a regular, repeating pattern, or may be delivered using complex patterns of pulses that appear to be irregular. Other parameters that may be controlled or varied include the amplitude, pulse width, and rate (or frequency) of the electrical pulses. Each electrode configuration, along with the electrical pulse parameters, can be referred to as a "modulation parameter set." Each set of modulation parameters, including allocated energy to the electrodes which may be provided as a fractionalized current distribution to the electrodes (as percentage cathodic current, percentage anodic current, or off), may be stored and combined into a modulation program that can then be used to modulate multiple regions within the patient.

The number of electrodes available combined with the ability to generate a variety of complex electrical waveforms (e.g. pulses), presents a huge selection of modulation parameter sets to the clinician or patient. For example, if the neuromodulation system to be programmed has sixteen electrodes, millions of modulation parameter sets may be available for programming into the neuromodulation system. Furthermore, for example SCS systems may have thirty-two electrodes which exponentially increases the number of modulation parameters sets available for programming. To facilitate such selection, the clinician generally programs the modulation parameters sets through a computerized programming system to allow the optimum modulation parameters to be determined based on patient feedback or other means and to subsequently program the desired modulation parameter sets.

Figure 4:
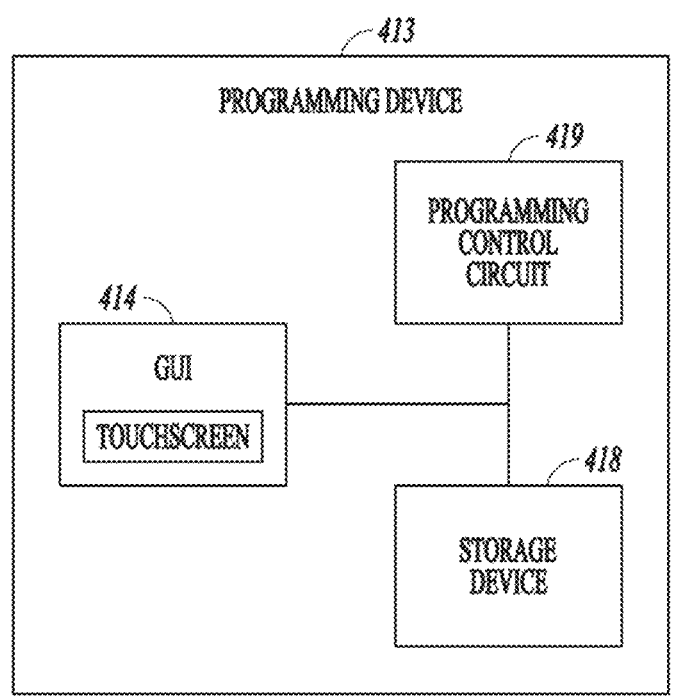
FIG. 4 illustrates, by way of example, an embodiment of a programming system such as a programming device, which may be implemented as the programming device in the neuromodulation system of FIG. 2.

FIG. 4 illustrates an embodiment of a programming system such as a programming device 413, which may be implemented as the programming device 213 in the neuromodulation system of FIG. 2. The programming device 413 may include a storage circuit 418, a programming control circuit 419, and a GUI 414. The programming control circuit 419 may generate the plurality of modulation parameters that controls the delivery of the neuromodulation pulses according to the pattern of the neuromodulation pulses. In various embodiments, the GUI 414 includes any type of presentation device, such as interactive or non-interactive screens, and any type of user input devices that allow the user to program the modulation parameters, such as touchscreen, keyboard, keypad, touchpad, trackball, joystick, and mouse. The storage circuitry 418 may store, among other things, modulation parameters to be programmed into the modulation device. The programming device 413 may transmit the plurality of modulation parameters to the modulation device. In some embodiments, the programming device 413 may transmit power to the modulation device. The programming control circuit 419 may generate the plurality of modulation parameters. In various embodiments, the programming control circuit 419 may check values of the plurality of modulation parameters against safety rules to limit these values within constraints of the safety rules.

In various embodiments, circuits of neuromodulation, including its various embodiments discussed in this document, may be implemented using a combination of hardware, software and firmware. For example, the circuit may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 5:
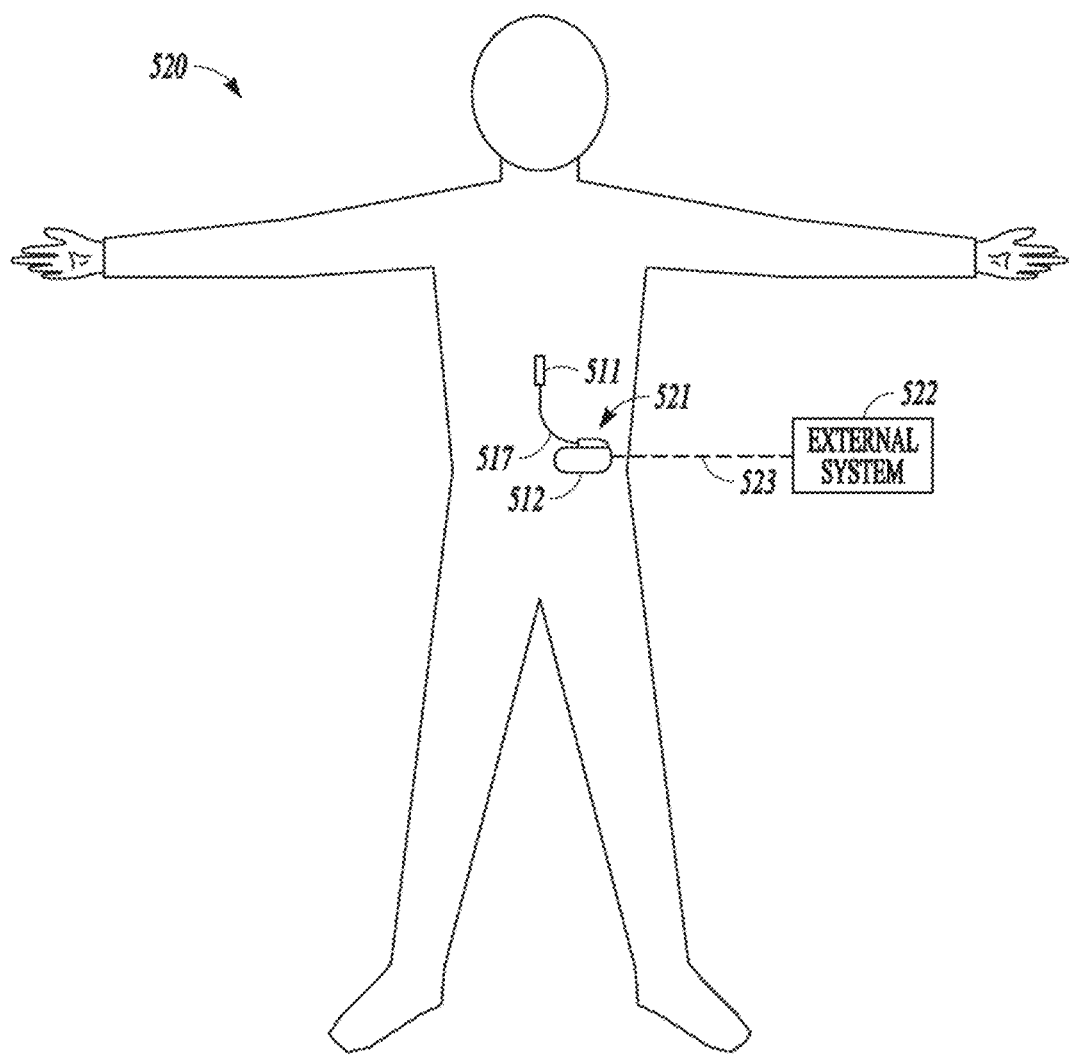
FIG. 5 illustrates, by way of example, an implantable neuromodulation system and portions of an environment in which system may be used.

FIG. 5 illustrates, by way of example, an implantable neuromodulation system and portions of an environment in which system may be used. The system is illustrated for implantation near the spinal cord. However, the neuromodulation system may be configured to modulate other neural targets. The system 520 may include an implantable system 521, an external system 522, and a telemetry link 523 providing for wireless communication between implantable system 521 and external system 522. The implantable system is illustrated as being implanted in the patient's body. The implantable system 521 includes an implantable modulation device (also referred to as a waveform generator or an implantable pulse generator, or IPG) 512, a lead system 517, and electrodes 511. The lead system 517 includes one or more leads each configured to be electrically connected to the modulation device 512 and a plurality of electrodes 511 distributed in the one or more leads. In various embodiments, the external system 522 includes one or more external (non-implantable) devices each allowing a user (e.g. a clinician or other caregiver and/or the patient) to communicate with the implantable system 521. In some embodiments, the external system 522 includes a programming device intended for a clinician or other caregiver to initialize and adjust settings for the implantable system 521 and a remote control device intended for use by the patient. For example, the remote control device may allow the patient to turn a therapy on and off and/or adjust certain patient-programmable parameters of the plurality of modulation parameters.

The neuromodulation lead(s) of the lead system 517 may be placed adjacent, i.e., resting near, or upon the dura, adjacent to the spinal cord area to be stimulated. For example, the neuromodulation lead(s) may be implanted along a longitudinal axis of the spinal cord of the patient. Due to the lack of space near the location where the neuromodulation lead(s) exit the spinal column, the implantable modulation device 512 may be implanted in a surgically-made pocket either in the abdomen or above the buttocks, or may be implanted in other locations of the patient's body. The lead extension(s) may be used to facilitate the implantation of the implantable modulation device 512 away from the exit point of the neuromodulation lead(s).

Figure 6:
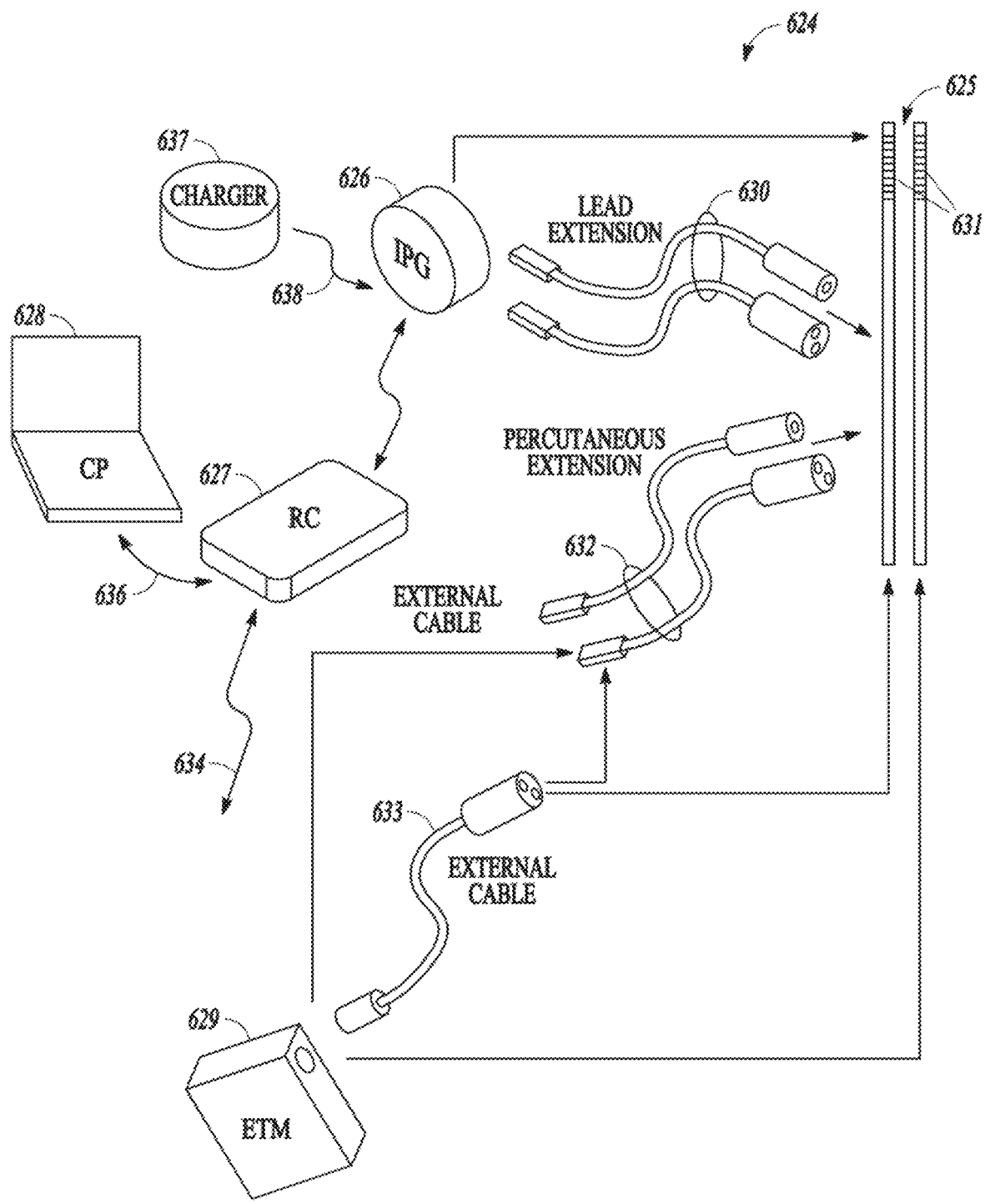
FIG. 6 illustrates, by way of example, an embodiment of a SCS system, which also may be referred to as a Spinal Cord Modulation (SCM) system.

FIG. 6 illustrates, by way of example, an embodiment of a SCS system, which also may be referred to as a Spinal Cord Modulation (SCM) system. The SCS system 624 may generally include a plurality (illustrated as two) of implantable neuromodulation leads 625, an electrical waveform generator 626, an external remote controller RC 627, a clinician's programmer (CP) 628, and an external trial modulator (ETM) 629. IPGs are used herein as an example of the electrical waveform generator. The waveform generator may be configurable to deliver repeating patterns of pulses, irregular patterns of pulses where pulses have differing amplitudes, pulse widths, pulse intervals, and bursts with differing number of pulses. The waveform generator may be configurable to deliver electrical waveforms other than pulses. The waveform generator 626 may be physically connected via one or more percutaneous lead extensions 630 to the neuromodulation leads 625, which carry a plurality of electrodes 631. As illustrated, the neuromodulation leads 625 may be percutaneous leads with the electrodes arranged in-line along the neuromodulation leads. Any suitable number of neuromodulation leads can be provided, including only one, as long as the number of electrodes is greater than two (including the waveform generator case function as a case electrode) to allow for lateral steering of the current. Alternatively, a surgical paddle lead can be used in place of one or more of the percutaneous leads. In some embodiments, the waveform generator 626 may include pulse generation circuitry that delivers electrical modulation energy in the form of a pulsed electrical waveform (i.e., a temporal series of electrical pulses) to the electrodes in accordance with a set of modulation parameters.

The ETM 629 may also be physically connected via the percutaneous lead extensions 632 and external cable 633 to the neuromodulation leads 625. The ETM 629 may have similar waveform generation circuitry as the waveform generator 626 to deliver electrical modulation energy to the electrodes accordance with a set of modulation parameters. The ETM 629 is a non-implantable device that is used on a trial basis after the neuromodulation leads 625 have been implanted and prior to implantation of the waveform generator 626, to test the responsiveness of the modulation that is to be provided. Functions described herein with respect to the waveform generator 626 can likewise be performed with respect to the ETM 629.

The RC 627 may be used to telemetrically control the ETM 629 via a bi-directional RF communications link 634. The RC 627 may be used to telemetrically control the waveform generator 626 via a bi-directional RF communications link 635. Such control allows the waveform generator 626 to be turned on or off and to be programmed with different modulation parameter sets. The waveform generator 626 may also be operated to modify the programmed modulation parameters to actively control the characteristics of the electrical modulation energy output by the waveform generator 626. A clinician may use the CP 628 to program modulation parameters into the waveform generator 626 and ETM 629 in the operating room and in follow-up sessions.

The CP 628 may indirectly communicate with the waveform generator 626 or ETM 629, through the RC 627, via an IR communications link 636 or other link. The CP 628 may directly communicate with the waveform generator 626 or ETM 629 via an RF communications link or other link (not shown). The clinician detailed modulation parameters provided by the CP 628 may also be used to program the RC 627, so that the modulation parameters can be subsequently modified by operation of the RC 627 in a stand-alone mode (i.e., without the assistance of the CP 628). Various devices may function as the CP 628. Such devices may include portable devices such as a lap-top personal computer, mini-computer, personal digital assistant (PDA), tablets, phones, or a remote control (RC) with expanded functionality. Thus, the programming methodologies can be performed by executing software instructions contained within the CP 628. Alternatively, such programming methodologies can be performed using firmware or hardware. In any event, the CP 628 may actively control the characteristics of the electrical modulation generated by the waveform generator 626 to allow the desired parameters to be determined based on patient feedback or other feedback and for subsequently programming the waveform generator 626 with the desired modulation parameters. To allow the user to perform these functions, the CP 628 may include a user input device (e.g., a mouse and a keyboard), and a programming display screen housed in a case. In addition to, or in lieu of, the mouse, other directional programming devices may be used, such as a trackball, touchpad, joystick, touch screens or directional keys included as part of the keys associated with the keyboard. An external device (e.g. CP) may be programmed to provide display screen(s) that allow the clinician to, among other functions, to select or enter patient profile information (e.g., name, birth date, patient identification, physician, diagnosis, and address), enter procedure information (e.g., programming/follow-up, implant trial system, implant waveform generator, implant waveform generator and lead(s), replace waveform generator, replace waveform generator and leads, replace or revise leads, explant, etc.), generate a pain map of the patient, define the configuration and orientation of the leads, initiate and control the electrical modulation energy output by the neuromodulation leads, and select and program the IPG with modulation parameters in both a surgical setting and a clinical setting.

An external charger 637 may be a portable device used to transcutaneously charge the waveform generator via a wireless link such as an inductive link 638. Once the waveform generator has been programmed, and its power source has been charged by the external charger or otherwise replenished, the waveform generator may function as programmed without the RC or CP being present.

FIG. 7 illustrates, by way of example, some features of the neuromodulation leads 725 and a waveform generator 726. The waveform generator 726 may be an implantable device or may be an external device such as may be used to test the electrodes during an implantation procedure. In the illustrated example, one of the neuromodulation leads has eight electrodes (labeled E1-E8), and the other neuromodulation lead has eight electrodes (labeled E9-E16). The actual number and shape of leads and electrodes may vary for the intended application. An implantable waveform generator may include an outer case for housing the electronic and other components. The outer case may be composed of an electrically conductive, biocompatible material, such as titanium, that forms a hermetically-sealed compartment wherein the internal electronics are protected from the body tissue and fluids. In some cases, the outer case may serve as an electrode (e.g. case electrode). The waveform generator may include electronic components, such as a controller/processor (e.g., a microcontroller), memory, a battery, telemetry circuitry, monitoring circuitry, modulation output circuitry, and other suitable components known to those skilled in the art. The microcontroller executes a suitable program stored in memory, for directing and controlling the neuromodulation performed by the waveform generator. Electrical modulation energy is provided to the electrodes in accordance with a set of modulation parameters programmed into the pulse generator. By way of example but not limitation, the electrical modulation energy may be in the form of a pulsed electrical waveform. Such modulation parameters may comprise electrode combinations, which define the electrodes that are activated as anodes (positive), cathodes (negative), and turned off (zero), percentage of modulation energy assigned to each electrode (which may also be referred to as allocated energy or fractionalized electrode configurations), and electrical pulse parameters, which define the pulse amplitude (measured in milliamps or volts depending on whether the pulse generator supplies constant current or constant voltage to the electrode array), pulse width (measured in microseconds), pulse rate (measured in pulses per second), and burst rate (measured as the modulation on duration X and modulation off duration Y). Electrodes that are selected to transmit or receive electrical energy are referred to herein as "activated," while electrodes that are not selected to transmit or receive electrical energy are referred to herein as "non-activated."

Electrical modulation occurs between or among a plurality of activated electrodes, one of which may be the case of the waveform generator. The system may be capable of transmitting modulation energy to the tissue in a monopolar or multipolar (e.g., bipolar, tripolar, or more than three poles) fashion. Monopolar modulation occurs when a selected one of the lead electrodes is activated along with the case of the waveform generator, so that modulation energy is transmitted between the selected electrode and case. Any of the electrodes E1-E16 and the case electrode may be assigned to up to k possible groups or timing "channels." In one embodiment, k may equal four. The timing channel identifies which electrodes are selected to synchronously source or sink current to create an electric field in the tissue to be stimulated. Amplitudes and polarities of electrodes on a channel may vary. In particular, the electrodes can be selected to be positive (anode, sourcing current), negative (cathode, sinking current), or off (no current) polarity in any of the k timing channels. The waveform generator may be operated in a mode to deliver electrical modulation energy that is therapeutically effective and causes the patient to perceive delivery of the energy (e.g. therapeutically effective to relieve pain with perceived paresthesia), and may be operated in a sub-perception mode to deliver electrical modulation energy that is therapeutically effective and does not cause the patient to perceive delivery of the energy (e.g. therapeutically effective to relieve pain without perceived paresthesia).

The waveform generator may be configured to individually control the magnitude of electrical current flowing through each of the electrodes. For example, a current generator may be configured to selectively generate individual current-regulated amplitudes from independent current sources for each electrode. In some embodiments, the pulse generator may have voltage regulated outputs. While individually programmable electrode amplitudes are desirable to achieve fine control, a single output source switched across electrodes may also be used, although with less fine control in programming. Neuromodulators may be designed with mixed current and voltage regulated devices.

The energy may be allocated to electrodes to provide a desired modulation field. Some non-limiting examples of modulation fields are provided below.

FIGS. 8-11 illustrate, by way of example, a difference in electrical field strength in the longitudinal and transverse directions when the current is fractionalized such that the electrical field in the longitudinal direction generated by the fractionalized current delivered to each electrode is approximately equal. The voltage at a patient's spinal cord (especially at the DC fibers) is approximately equal in the longitudinal direction, resulting in a voltage gradient of approximately zero along the DC. This may require different amounts of allocated energy to each electrode (e.g. fractionalized current delivered to each electrode). Calibration techniques are used to determine the proper current fractionalization. With the current fractionalized to a plurality of electrodes on the electrical modulation lead, the resulting field can be calculated by superimposing the fields generated by the current delivered to each electrode. Moreover each electrical field has a longitudinal component and a transverse component.

FIG. 8 is a schematic view of a single electrical modulation lead 839 implanted over approximately the longitudinal midline of the patient's spinal cord 840. It is understood that additional leads or lead paddle(s) may be used, such as may be used to provide a wider electrode arrangement and/or to provide the electrodes closer to dorsal horn elements, and that these electrode arrays also may implement fractionalized current. FIG. 9 illustrates an embodiment where an electrical modulation lead 941 has been implanted more laterally with respect to the spinal cord, thereby placing it proximate the dorsal horn of the spinal cord, and the other electrical modulation lead 942 has been implanted more medially with respect to the spinal cord, thereby placing it proximate the dorsal column of the spinal cord 940. Placement of the lead more proximate to the DH than the DC may be desirable to preferentially stimulate DH elements over DC neural elements for a sub-perception therapy. Any other plurality of leads or a multiple column paddle lead can also be used. Longitudinal component of the electrical field is directed along the y-axis depicted in FIG. 8, and a transverse component of the electrical field is directed along the x-axis depicted in FIG. 8. Some embodiments may include directional leads with one or more directional electrodes. A directional electrode may extend less than 360 degrees about the circumference of a lead body. For example, a row of two or more directional electrodes (e.g. "segmented electrodes") may be positioned along the circumference of the lead body. Activating select ones of the segmented electrodes may help extend and shape the field in a preferred direction.

Figure 10:
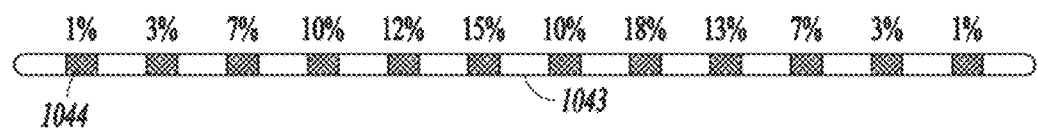
FIG. 10 is a schematic view of the electrical modulation lead showing an example of the fractionalization of the anodic current delivered to the electrodes on the electrical modulation lead.

FIG. 10 is a schematic view of the electrical modulation lead 1043 showing an example of the fractionalization of the anodic current delivered to the electrodes on the electrical modulation lead. In order to provide a simpler illustration, these figures illustrate fractionalization using monopolar modulation where a case electrode of the waveform generator is the only cathode, and carries 100% of the cathodic current. The fractionalization of the anodic current shown in FIG. 10 does not deliver an equal amount of current to each electrode 1044, because this embodiment takes into account electrode/tissue coupling differences, which are the differences in how the tissue underlying each electrode reacts to electrical modulation. Also, the ends of the portion of the electrical modulation lead include electrodes having lower gradient in the longitudinal direction. The magnitude of the electrical field tapers down at the ends of the electrical modulation lead. Fractionalization of the current to the electrodes is controlled such that the tissue underlying each electrode in the middle portion of the electrical modulation lead reacts approximately equally to the electrical modulation, or tissue activation underlying each electrode are eliminated. However, the resulting fractionalization is not equal. In the embodiment shown in FIG. 10, fractionalization of the current to the middle electrodes varies from 10% to 18%, reflecting the variation in the tissue underlying those electrodes. The fractionalization across the electrical modulation lead can vary in any manner as long as the total of fractionalized currents equals 100%. Various embodiments described herein implement a programmed algorithm to determine the appropriate fractionalization to achieve a desired modulation field property (e.g. constant electric field, or constant electric field magnitude, or constant voltage). Furthermore, as discussed in more detail below the allocation of energy to the electrodes for the target pole may be further improved using space domain scaling to compensate for patient-specific displacement between electrodes or between electrode and tissue, and/or using time domain scaling to account for at least one property of a neural target or of a neuromodulation waveform.

Figure 11:
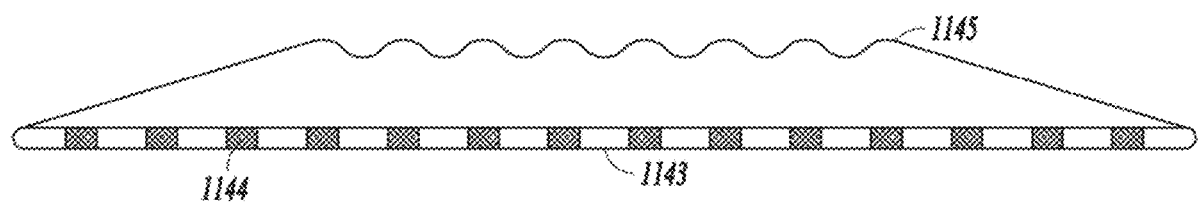
FIG. 11 illustrates, by way of example, a schematic illustration of a gradient in the longitudinal direction along the axis of the electrical modulation lead.

FIG. 11 illustrates, by way of example and not limitation, a schematic illustration of a gradient that may exist in the longitudinal direction along the axis of the electrical modulation lead. The electrical field strength 1145 in the longitudinal direction is plotted over a schematic representation of the electrodes 1144 on the electrical modulation lead 1143. The illustration in FIG. 11 shows that the electrical field strength is substantially constant over the middle portion of the electrical modulation lead, but may form a wave with very small amplitude because of the gaps between the electrodes in the lead. This substantially constant electrical field forms a small longitudinal gradient, which minimizes activation of the large myelinated axons in the dorsal column. The illustration in FIG. 11 also shows the electrical field in the longitudinal direction tapering at the ends of the electrical modulation lead.

Figure 12:
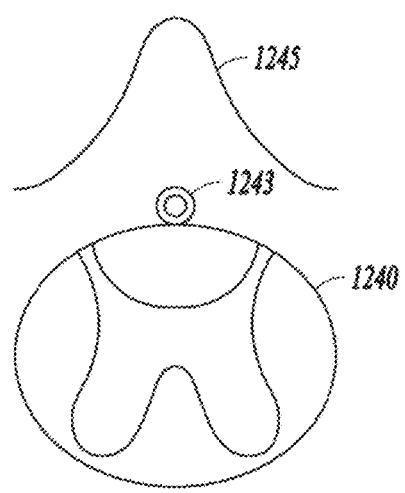
FIG. 12 illustrates, by way of example, a schematic illustration of a gradient in the transverse direction.

FIG. 12 illustrates, by way of example, a schematic illustration of a gradient that may exist in the transverse direction. The transverse electrical field strength 1245 in the transverse direction is plotted over a schematic representation of the electrical modulation lead 1243 and the spinal cord 1240 of the patient. The illustration in FIG. 12 shows that the transverse electrical field strength is greatest adjacent the electrical modulation lead and falls off lateral of the electrical modulation lead. Use of additional modulation leads to widen the electrode array may be used to provide desired fractionalization to also provide a region of a substantially constant electric field for a distance along the transverse direction. Substantially constant electric fields may favor modulation of dorsal horn and/or dorsal root neuronal elements over dorsal column neuronal elements. Various embodiments may use a substantially constant electric field to target inhibitory interneurons that propagate in anterior-posterior direction.

Figure 13:
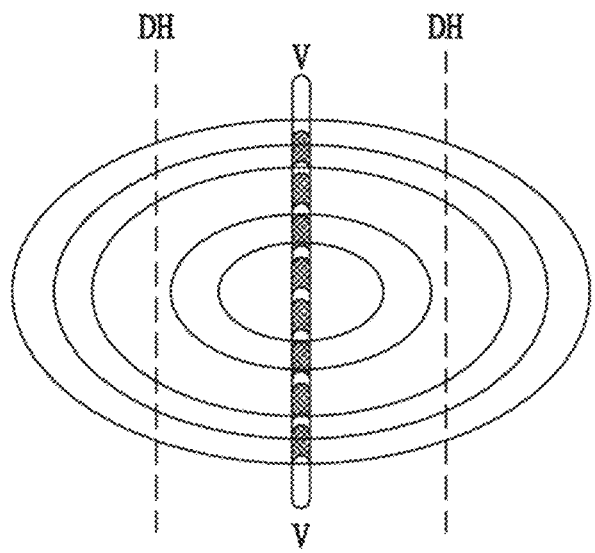
FIG. 13 illustrates, by way of example, equipotential voltage lines for a lead, along with a representation of the lead and the dorsal horns.
Figure 14:
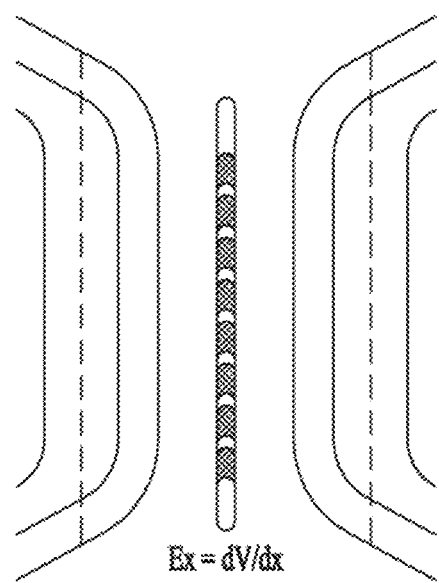
FIGS. 14-15 illustrate, by way of example, a substantial uniform electric field, along with a representation of the lead and the dorsal horns.
Figure 15:
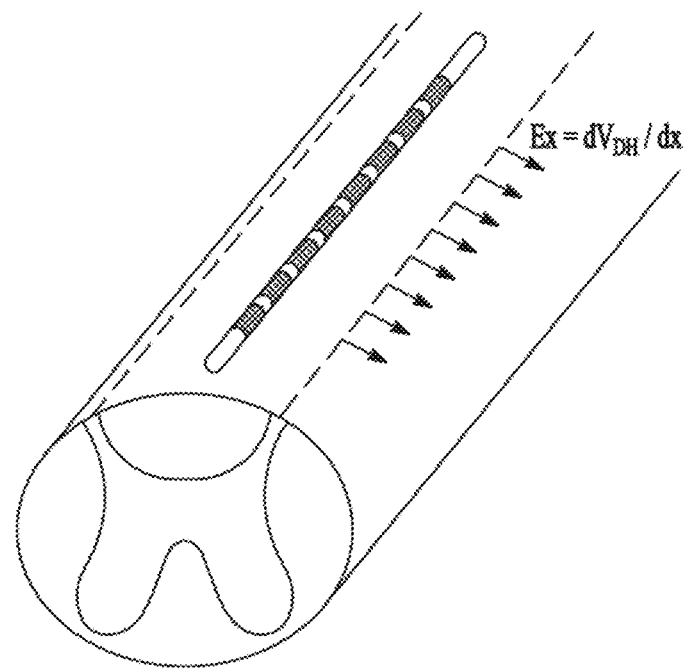

FIG. 13 illustrates, by way of example, equipotential voltage lines for a lead, along with a representation of the lead and the dorsal horns; and FIGS. 14-15 illustrate, by way of example, a substantial uniform electric field, along with a representation of the lead and the dorsal horns. The orientation of the electrical field may be selected to target the different directions/orientations of the DH elements. To generate electrical fields in different medio-lateral directions, the electrodes may have different current fractionalizations in the radial direction.

The SCS system may be configured to deliver different electrical fields to achieve a temporal summation of modulation in the DH elements. For embodiments that use a pulse generator, the electrical fields can be generated respectively on a pulse-by-pulse basis. For example, a first electrical field can be generated by the electrodes (using a first current fractionalization) during a first electrical pulse of the pulsed waveform, a second different electrical field can be generated by the electrodes (using a second different current fractionalization) during a second electrical pulse of the pulsed waveform, a third different electrical field can be generated by the electrodes (using a third different current fractionalization) during a third electrical pulse of the pulsed waveform, a fourth different electrical field can be generated by the electrodes (using a fourth different current fractionalized) during a fourth electrical pulse of the pulsed waveform, and so forth. These electrical fields may be rotated or cycled through multiple times under a timing scheme, where each field is implemented using a timing channel. The electrical fields may be generated at a continuous pulse rate, or may be bursted on and off. Furthermore, the interpulse interval (i.e., the time between adjacent pulses), pulse amplitude, and pulse duration during the electrical field cycles may be uniform or may vary within the electrical field cycle.

An embodiment may modify the fractionalized current delivered to each electrode to minimize the electrical field gradient in the longitudinal direction, so as to minimize activation of the DC elements. Minimizing activation of the DC elements can include a model-based calculation, where the model includes the information from the calibration. A discrete activating function can be calculated by the formula: $AF(n)=Ga/(\pi \times d \times 1) \times [Ve(n-1)-2\ Ve(n)+Ve(n+1)]$, wherein Ga is the axonal intermodal conductance, d is the axonal diameter, 1 is the length of the node of Ranvier, Ve(n) is the strength of the electric field at the node for which the activating function is determined, Ve(n−1) is the strength of the electric field at the node preceding the node for which the activating function is determined, and Ve(n+1) is the strength of the electric field at the node following the node for which the activating function is determined. Using this formula, the discrete activating function is calculated from the conductance normalized to the surface area of the node of Ranvier.

Modulation thresholds vary from patient to patient and from electrode to electrode within a patient. An electrode/tissue coupling calibration of the physical electrodes may be performed to account for these different modulation thresholds and provide a more accurate fractionalization of the current between electrodes. For example, perception threshold may be used to normalize the physical electrodes. The RC or the CP may be configured to prompt the patient to actuate a control element, once paresthesia is perceived by the patient. In response to this user input, the RC or the CP may be configured to respond to this user input by storing the modulation signal strength of the electrical pulse train delivered when the control element is actuated. Other sensed parameter or patient-perceived modulation values (e.g. constant paresthesia, or maximum tolerable paresthesia) may be used to provide the electrode/tissue coupling calibration of the physical electrodes. These sensed parameter or patient-perceived modulation values may be used to estimate the current fractionalization by minimizing the sum of the square of the discrete activating function divided by the determined value (e.g. perception threshold) at each physical electrode on an electrical modulation lead as is described in more detail below. Squaring the discrete activating function, or any driving force from the electrical field, eliminates the differences in depolarizing and hyperpolarizing fields. The current fractionalization that results in a minimize sum minimizes the field gradient in the longitudinal direction.

Various embodiments of the present subject matter may use "target multipoles." For example, target multipoles may be used to provide a linear field that may maximize the electric field in a region while minimizing the activation of dorsal columns. These target multipoles may be referred to as "ideal" or "virtual" multipoles. Each target pole of a target multipole may correspond to one physical electrode, but may also correspond to a space that does not correspond to one electrode, and may be emulated using electrode fractionalization. By way of examples, U.S. Pat. Nos. 8,412,345 and 8,909,350 describe target multipoles. U.S. Pat. Nos. 8,412,345 and 8,909,350 are hereby incorporated by reference in their entirety. Target multipoles are briefly described herein.

A stimulation target in the form of a target poles (e.g., a target multipole such as a target bipole or target tripole or a target multipole with more than three target poles) may be defined and the stimulation parameters, including the allocated energy values (e.g. fractionalized current values) on each of the electrodes, may be computationally determined in a manner that emulates these target poles. Current steering may be implemented by moving the target poles about the leads, such that the appropriate allocated energy values (e.g. fractionalized current values) for the electrodes are computed for each of the various positions of the target pole.

Figure 16A:
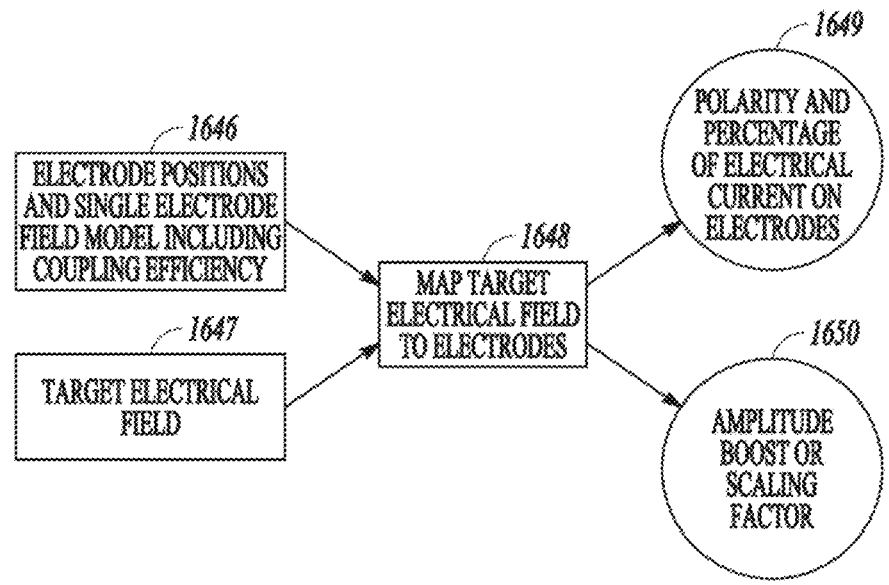
FIG. 16A illustrates, by way of example, mapping of target electrical fields to electrodes.

With reference to FIG. 16A, the CP may be configured to accept relative electrode positions as well as a single electrode field model including coupling efficiency 1646 and a representation of a target electrical field 1647 (instead of including these parameters in the design of navigation tables) and to map the target electrical field to the electrodes 1648, thereby yielding energy allocation (e.g. the polarities and percentages of electrical current to be associated with the electrodes 1649), as well as a boost or scaling factor 1650 for globally adjusting the magnitude of the total energy (e.g. current) supplied to the electrodes. Electrode locations and information about the desired electrical field may be independently inputted into the algorithm.

Figure 16B:
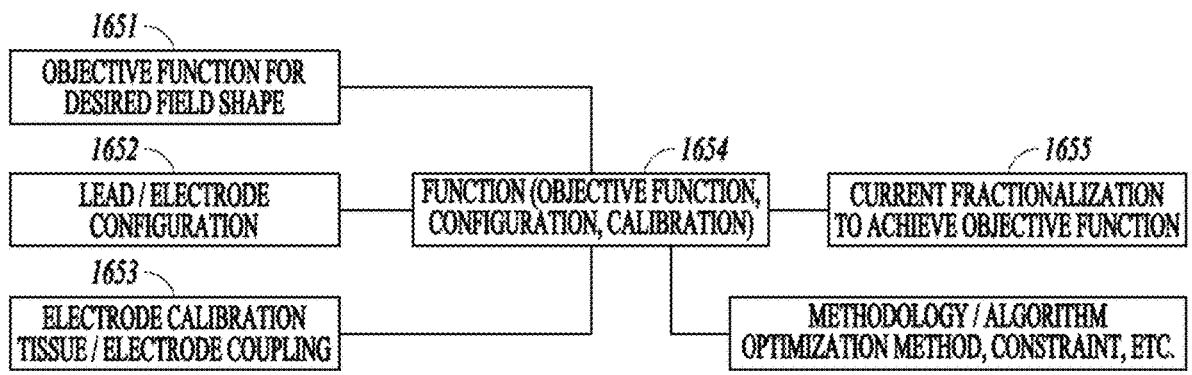
FIG. 16B illustrates, by way of example, an embodiment for determining fractionalization to achieve an objective function.

FIG. 16B illustrates, by way of example, an embodiment for determining energy allocation (e.g. current fractionalization) to achieve an objective function. An objective function refers to a function with desirable characteristics for modulating the targeted tissue. The objective function may also be referred to as an objective target function. An objective function 1651 for a desired field shape may be identified for a given volume of tissue. By way of example and not limitation, an objective function may provide a broad and uniform modulation field such as a constant E (electric field), a constant |E| (electric field magnitude), and a constant voltage. The lead and electrode configuration 1652 are also identified, as well as calibration for the physical electrode-to-tissue coupling 1653. A function 1654 is performed that is dependent on the objective function, the lead and electrode configuration and the calibration. The function 1654 may also be dependent on other inputs (e.g. a methodology/algorithm, an optimization method, a constraint, and the like). The result of the function is the allocation of modulation energy (e.g. current fractionalization) 1655 for each electrode to achieve the objective function.

Figure 17:
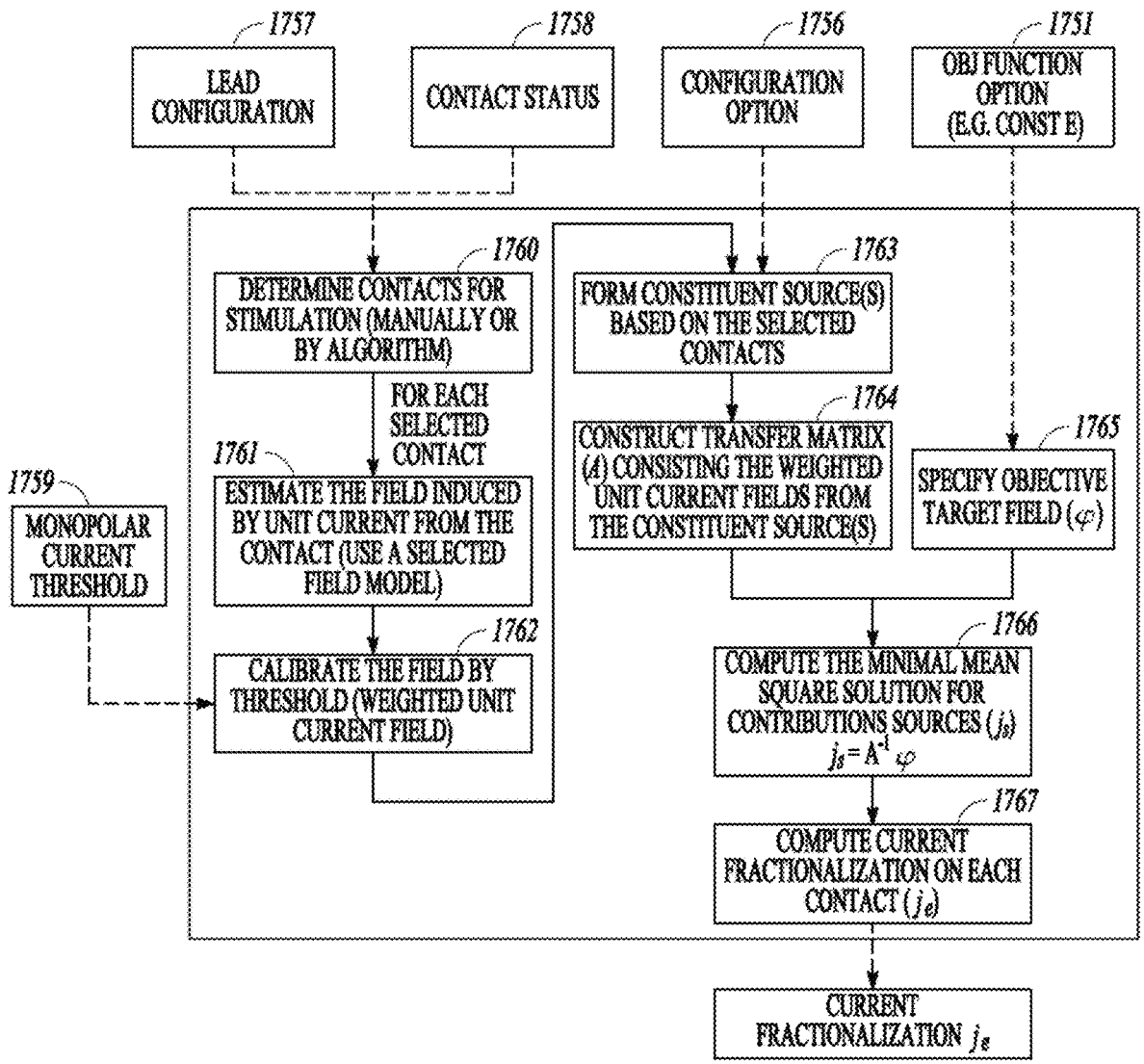
FIG. 17 illustrates, by way of example, an embodiment for determining fractionalization to achieve an objective function with more detail.

FIG. 17 illustrates, by way of example, an embodiment for determining energy allocation (e.g. current fractionalization) to achieve an objective function with more detail. An objective target function 1751 (e.g. constant E) is provided as an input to a process. Other inputs to the process include a configuration option 1756, a lead configuration 1757 and electrode contact status 1758, and a threshold 1759 such as a current threshold or more particularly a monopolar current threshold. The lead configuration 1757 and contact status 1758 identify an electrode arrangement, identifying a position of each electrode to determine the field. The overall field is a superimposed field from each electrode. The configuration option 1756 refers to monopolar (same polarity for all activated electrodes) and multipolar options (combined anode and cathodes in field). The threshold is used to compensate for electrode/tissue coupling differences.

The contacts for stimulation may be determined automatically or manually 1760 from the lead configuration and contact status. A selected field model may be used to estimate the field induced by unit current from the contact 1761. The field is calibrated using the threshold 1762. For example, the unit current field may be weighted. Constituent sources are formed based on the selected contacts 1763, and a transfer matrix 1764 is constructed to use to compute the minimal mean square solution 1766 using contributions from the constituent sources and using a specified target field 1765. The solution can be used to compute the current fractionalization on each contact 1767.

With reference to FIGS. 18A-18B, the CP may map a target electrical field to the electrode array by estimating the field potential values (or some other linear electrical parameter, such as an activating function, current density, etc.) of the target field at a plurality of spatial observation points. The CP may accomplish this by determining the desired locations of target current source poles relative to the electrode array, and modeling an electrical field generated by the target current source poles to determine desired field potential values at the spatial observation points (e.g., using analytical and/or numerical models).

Although target current source poles are one way to represent a "target electrical field", other representations of target fields may be used. The locations of the target current source poles may be determined in a manner that places the resulting electrical field over an identified region of the patient to be stimulated. The spatial observation points may be spaced in a manner that would, at the least, cover the entire tissue region to be stimulated and/or a tissue region that should not be stimulated. The locations of the target current source poles may be defined by the user, and may be displayed to the user along with the electrode locations, which as briefly discussed above, may be determined based on electrical measurements taken at the electrodes. Referring to FIGS. 19A-19C, the CP may select, or allow a user to select, a plurality of constituent current sources at the locations of the electrodes. The locations of the electrodes may be determined based on measurements taken at the electrodes in response to sub-threshold electrical signals transmitted between the electrodes. In the illustrated target bipole a first constituent current source can be defined at the locations of electrodes E1 and E2 as −100% and +100%, respectively (FIG. 19A); a second constituent current source can be defined at the locations of electrodes E2 and E3 as −100% and +100%, respectively (FIG. 19B); a third constituent current source can be defined at the locations of electrodes E3 and E4 as −100% and +100%, respectively (FIG. 19C); and so on. It is noted that these figures are provided to an example of constituent sources. Other combinations can be used. It is further noted that the system may be designed to use voltage or current sources as the electrical sources in the constituent sources. The location of each of the electrodes is included within at least one of the constituent sources. Thus, the minimum number of constituent sources may be equal to the number of contacts less one, or may equal the number of contacts (e.g., if a monopole is used as the constituent source).

Once the constituent sources are selected, the CP may determine the relative strengths of the constituent current sources that, when combined, result in estimated electrical field potential values at the spatial observation points that best matches the desired field potential values at the spatial observation points. In particular, the CP may model the constituent current sources (e.g., using analytical and/or numerical models) and estimate the field potential values per unit current (V/mA) generated by each of the constituent current sources at the spatial observation points, and may generate an m×n transfer matrix (shown in FIG. 20) from the estimated field potential values per unit current, with m equaling the number of spatial observation points and n equaling the number of constituent sources. The relative strengths of the constituent current sources may be determined using an optimization function that includes the transfer matrix A and the desired field potential values. The above description uses field potential or voltage values as an example of parameter values that can be associated with each of the observation points. Other parameters may be used as well including derived parameters values such a derivative, activating function, total driving function, and the like.

The optimization function may be a least-squares (overdetermined) function expressed as: $|\varphi - A\hat{j}|2$, where $\varphi$ is an m-element vector of the desired electrical field parameter values (e.g. desired field potential values), A is the transfer matrix, and $\hat{j}$ is an n-element vector of the strengths of the constituent current sources. The constituent current source strengths $\hat{j}$ may be solved such that the optimization function $|\varphi - A\hat{j}|2$ is minimized. The square difference is minimized if $\varphi = A\hat{j}$. One approach for solving this problem may be to invert the transfer matrix A and pre-multiply, such that $A-1=\varphi A-1A\hat{j}$, which yields the solution $\hat{j}=A-1\varphi$. Once the strengths of the constituent current sources are determined, the CP converts these strengths to energy allocations (e.g. current distributions) on the electrodes in the form of a polarity and percentage.

The remainder of this document discusses various embodiments that relate to optimizing electrode configurations to be used with sub-perception SCS. The sub-perception SCS may include, but is not limited to, burst SCS, high rate SCS, long pulse width, and/or high density forms of SCS. The burst SCS may include 2 to 7 pulses wherein each burst of pulses may have a pulse frequency, also referred to as an intraburst pulse frequency, within a range between 250 Hz to 500 Hz. The burst-to-burst frequency (also referred to as an interburst frequency, may be within a range of 20 Hz to 60 Hz. High rate SCS may include SCS with a frequency equal to or greater than 1 kHz. Long pulse width SCS may include pulse widths of 90 microseconds or more for the active phase, rather than the total length of the waveform, of a pulse. High density forms of SCS may include SCS using high duty cycle or high "charge per phase" waveforms. A waveform may be defined as "high density" if charge delivered per unit time is above a threshold. By way of example and not limitation, waveforms may be considered to be "high density" if over 20% of the duty cycle consists of an active stimulation phase. A high density classification is based more on a duty cycle and/or a charge per time measurement rather than a pulse rate. For example, both a 500 Hz and a 1 kHz waveform may be defined as "high density" if the proportion of the duty cycle occupied by the active phase exceeds a threshold (e.g. 20% to 25%). Collectible patient feedback data may be used to provide a feedback metric used to optimize the energy allocations to electrodes (e.g. electrode fractionalizations) and total amplitudes to best match a user-specified target pole. Examples of such collectible feedback data may include, but are not limited to patient-provided paresthesia data (e.g. amplitude and sensation) such as may be used to identify paresthesia threshold, evoked action potentials (ECAPs) such as ECAPs representing activity in the dorsal roots, dorsal horn, and/or dorsal column, and Local Field Potentials (LFPs).

As discussed above, target poles with inverse modeling have been used to define electrode parameters for SCS. Additionally, U.S. Pat. No. 8,412,345, entitled "System and Method for Mapping Arbitrary Electric Fields to Pre-Existing Lead Electrodes" which is incorporated herein by reference in its entirety, discusses the use of target poles, which have also been referred to as "ideal" poles. Also, as discussed above and in U.S. Pat. Pub. No. 20160082251, entitled "Neuromodulation Specific to Objective Function of Modulation Field for Targeted Tissue" which is incorporated herein by reference in its entirety, target poles can be specified to provide field features to target neural elements.

However, real clinical outcomes depend on patient-to-patient differences in electrode-tissue coupling and neural excitability. For sub-perception modulation for which the patient does not perceive paresthesia or another indication of the delivered energy, patient feedback is not available for real-time adjustments to the modulation.

For example, electrode-tissue coupling may be affected by the cerebral spinal fluid (CSF) space, which may vary by patient and by the position along the spinal column. The patient-specific and position-specific differences in electrode-tissue coupling affect the field geometry. Various embodiments of the present subject matter provide space domain scaling to account for displacement (e.g. a distance in a given direction) between electrodes or between electrode and tissue. Also, different neural tissue exhibit different excitability to the same field. For example, synaptic terminals and axons have different excitability to modulation fields. Various embodiments of the present subject matter provide time domain scaling for targeted neural tissue. Various embodiments of the present subject matter may provide both space domain scaling and time domain scaling for targeted neural tissue.

Figure 21:
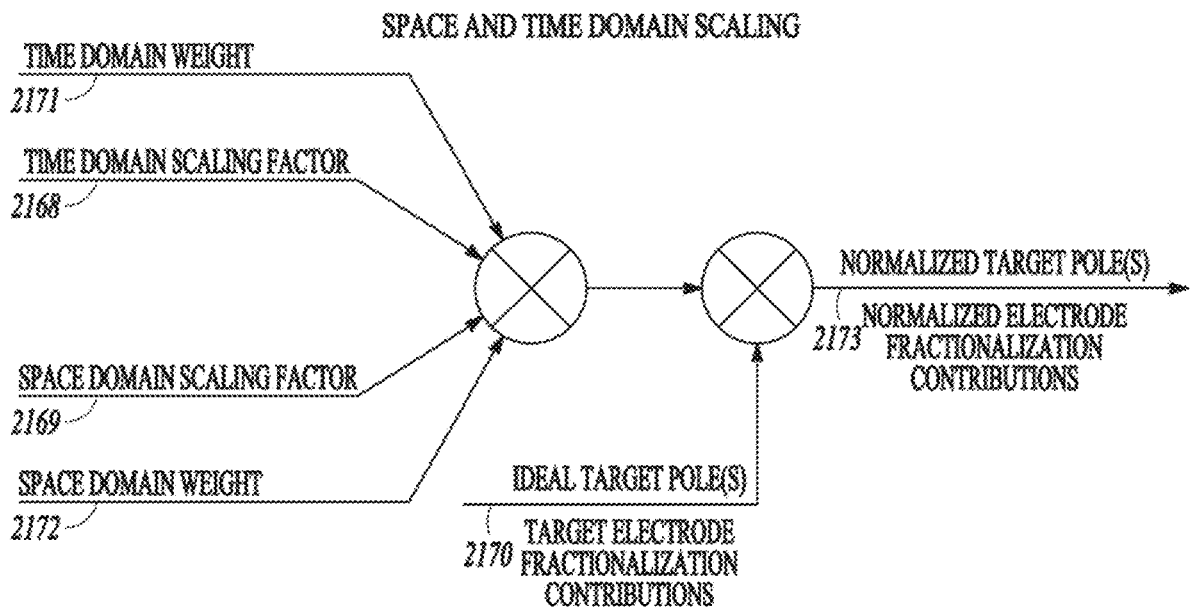
FIG. 21 illustrates, by way of example and not limitation, a diagram for scaling allocated energy for one or more ideal target poles using a time domain scaling factor and/or a space domain scaling factor.

FIG. 21 illustrates a diagram in which a time domain scaling factor 2168 and/or a space domain scaling factor 2169 are applied to allocated energy (e.g. target electrode fractionalization contributions) 2170 for one or more ideal target poles. The scaling factor(s) may serve as a multiplier to the allocated energy of each electrode. Further, a product of the time domain scaling factor and the space domain scaling factor may be applied to provide an overall scaling factor to allocated energy for the ideal target pole(s). Also, a time domain weight factor 2171 may be applied to the time domain scaling factor, and/or a space domain weight factor 2172 may be applied to the space domain scaling factor. The result of the scaling is normalized target pole(s) 2173, where allocated energy (e.g. electrode fractionalization contributions) are normalized to address differences in electrode-tissue coupling and/or neural excitability.

Space Domain Scaling

Figure 22:
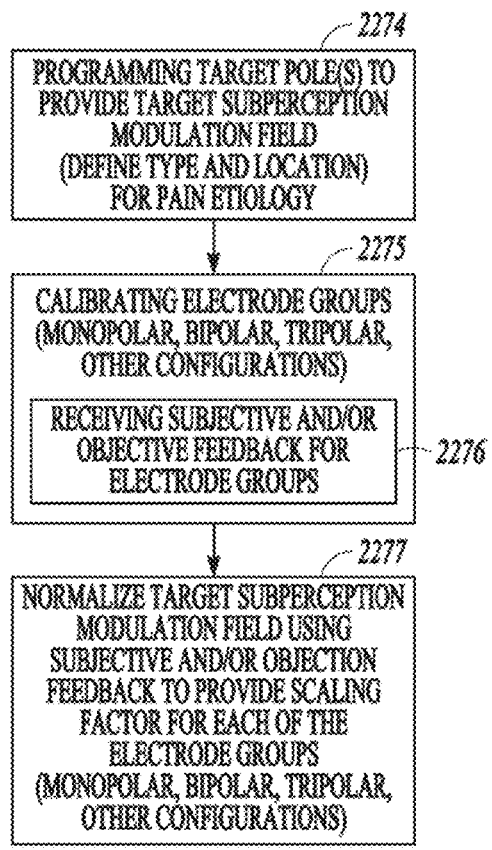
FIGS. 22 and 23A-23C illustrate, by way of example and not limitation, a process for programming a sub-perception target modulation field and normalizing the target modulation field to account for patient-to-patient differences in electrode-tissue coupling and/or neural excitability.

FIG. 22 illustrates a process for programming a sub-perception target modulation field and normalizing the target modulation field to account for patient-to-patient differences in electrode-tissue coupling and/or neural excitability. At 2274 target pole(s) to provide a target sub-perception modulation field may be programmed. For example, a physician or other user may define target pole(s), which can then be moved along the neural anatomy using electrodes operably positioned the neural anatomy. The defined target poles may be defined to provide a desired neuromodulation field (e.g., a dorsal horn stimulation ("DHS") field, a linear bipole, etc.). The physician or other user may define the location for the target pole(s) to provide the target sub-perception modulation field at a location based on pain etiology. This target sub-perception modulation field may be uniform across electrodes. In an example illustrated in FIG. 23A, the target poles are defined as three cathodes and three anodes on each lead.

At 2275, electrode groups in the electrode array(s) are calibrated. The electrode groups may be one electrode for monopolar stimulation, two electrodes for bipolar stimulation, three electrodes for tripolar stimulation, or multiple electrodes for multipolar stimulation. The ability to test specific electrode groups may be more accurate in determining the subjective and/or object responses to modulation fields that use more than one target poles. Each of the electrode groups to be tested, which may include one or more electrodes, may be turned on sequentially and/or cycled individually up to a stimulus setting (amplitude, pulse width, relevant stimulation frequency) that is sufficient to produce sensation for subject feedback or a biomarker for objective feedback. The cycling may be automatic or guided by a physician or other user. For example, a physician or other user may limit electrodes over which cycling will happen.

Figure 23C:
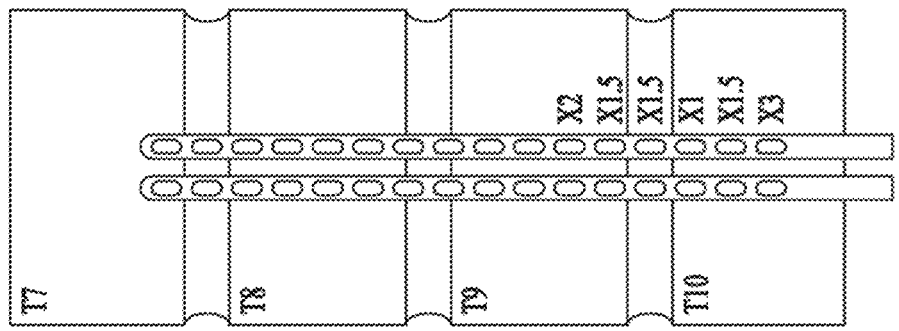
Figure 23B:
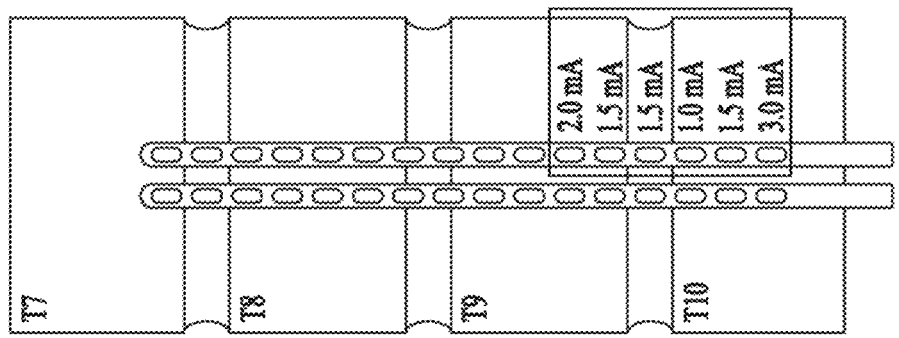
Figure 23A:
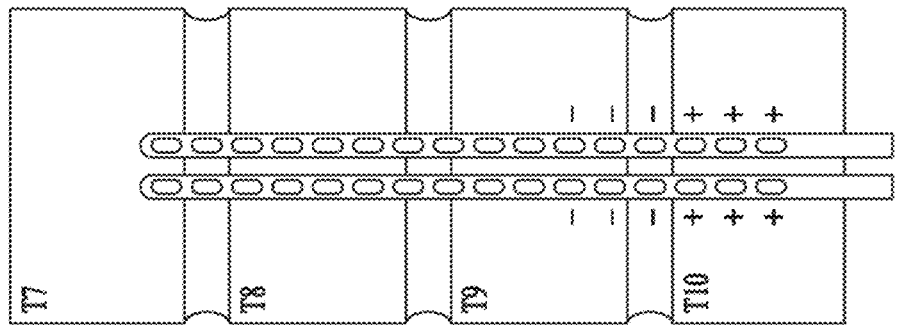

At 2276, subjective or objective feedback may be received to provide a patient-specific metric for the patient's response to the stimulation. Examples of such metrics may include but are not limited to tolerability or perception thresholds, and spatial distribution of the perception. An example of subjective feedback may include patient reports of paresthesia. Examples of objective feedback may include, but are not limited to, sensed evoked compound action potentials (ECAPs) over dorsal horn, local field potentials (LFPs), and dorsal root potential (indicating primary afferent depolarization) recorded by another electrode, biopotential templates, signal amplitudes, signal-to-noise ratio of electroneurograms (ENGs), and latency between stimulation artifact and evoked action potentials. One or more patient-specific metrics may be recorded for use in normalizing the target sub-perception modulation field. By way of example and not limitation, some metrics may include the lowest value, the highest value, the mean value or another aggregate value representing a quantitative output metric that may be user-defined or designed into the system. In an example illustrated in FIG. 23B, each electrode in the target poles for the right lead in FIG. 23A are tested, and the amplitude at which the sensation or biomarker is present is listed alongside of the electrode.

At 2277, the target sub-perception modulation field is normalized for the patient. The target pole(s) referenced in the calibration is calculated with the assumption that the patient' spinal cord is uniform and flat. Values for an electrode's contribution to the sub-perception modulation field may be scaled in proportion to the magnitude of the output metric that was recorded for that electrode. This adjustment may be further adjusted according to a user-specified or built-in neural target, the pulse width of stimulation, the frequency of stimulation, the waveform shape, or another stimulation-relevant factor (time domain scaling). In the example illustrated in FIG. 23C, the normalized scaling factor for each of the electrodes is illustrated alongside of the electrode in proportion to the magnitude of the amplitude at which the sensation or biomarker was present as illustrated in FIG. 23B.

Figure 24:
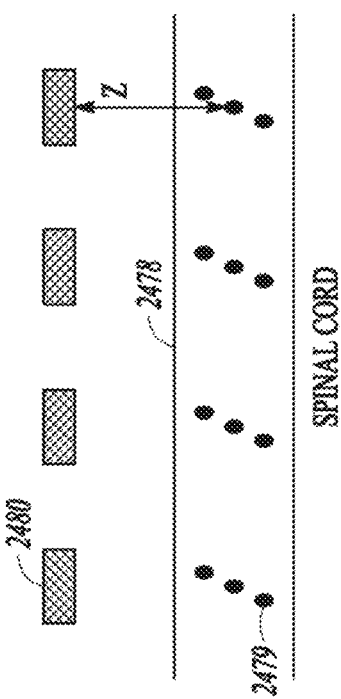
FIG. 24 illustrates a flat spinal cord with uniformly spaced observation points and with electrodes uniformly spaced from the spinal cord.

As discussed above, inverse modeling method matches potentials/fields/activation functions produced by an electrode configuration to potentials/fields/activating functions specified by an idealized target pole. The observation points are defined. Prior systems assumed a constant electrode tissue coupling efficiency by assuming a constant distance between the electrode contacts and the observation points. For example, the spinal cord and electrode arrays were uniform and straight. FIG. 24 illustrates a flat spinal cord 2478 with uniformly spaced observation points 2479 and with electrodes 2480 (illustrated as four electrodes although there may be more) uniformly spaced from the spinal cord.

Figure 25:
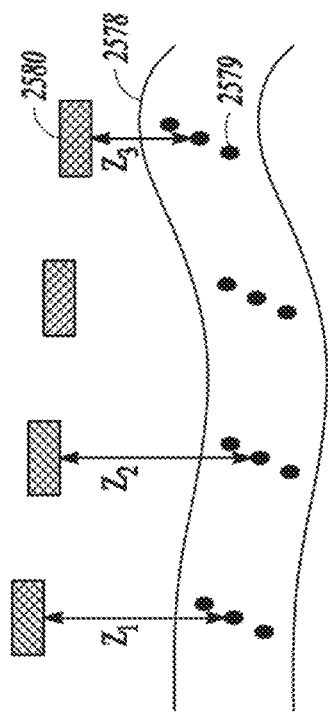
FIG. 25 illustrates a non-uniformly straight spinal cord with electrodes non-uniformly spaced from the spinal cord.

However, in reality, the electrode may not be fully aligned, the field may not be fully aligned, and/or the spinal cord is not perfectly straight. FIG. 25 illustrates a non-uniformly straight spinal cord 2578 with electrodes 2578 non-uniformly spaced from the spinal cord. The distances between the electrodes 2580 and the tissue vary, as represented by the different distances $Z1$, $Z2$ and $Z3$. Unlike prior systems, the present subject matter may recalculate or redefine the observation points 2579 based on tissue inhomogeneities.

Various embodiments may adjust the spatial observation points used to calculate the contributions of active electrodes to a target pole or to target poles such as target bipoles, target tripoles or other target multipoles. The adjustments to the spatial observation points 2579 may be based on characteristics of the target field and/or environment. For example, the adjustments to the spatial observation points 2579 may be based on the coupling strength between the neural tissue in the spinal cord 2578 and the electrode 2580 or patient-reported differences in paresthesia thresholds across electrode contacts.

FIG. 26A illustrates a calculated target field in the ideal environment in which the observation points 2679, which may be defined using a Cartesian coordinate system (x, y, z), are pre-set or placed/seeded according to the number of electrodes 2680 implanted and/or seeded for stimulation. In the example illustrated in FIG. 26A, the calculated target field in the ideal environment includes fractionalized electrode amplitudes for the cathodes of a target multipole that are given as percentages (75% and 25%), and fractionalized amplitudes for the anodes of the target multipole that are also given as percentages (−25% and −75%). These fractionalized electrode amplitudes appropriately allocate energy to provide a target cathode 2681 and target anode 2682. FIG. 26B illustrates a real spinal cord environment, which may be estimated during the calibration of the electrode groups using a feedback metric derived using objective and/or subjective measures. Each of the electrode groups may include one or more electrodes per group. The feedback metric may provide a scaling factor for the allocated energy at each electrode to normalize the field to the real spinal cord environment. In the example illustrated in FIG. 26B, the scaling factors for the electrodes may be 1.5×, 3.0×, 3.0× and 1.0×. A target field (+electrode fractionalizations) of arbitrary location and angle may be first calculated assuming the ideal environment. The spatial observation points may have voltage values $\Phi e(x,y,z)$, or longitudinal electric field values $E(x, y, z)$. Other derived values may also be used such as derivatives, activating functions, total driving functions and the like. Old values of $\Phi e$, $E$ are kept for a given spatial observation point, but the point coordinates are moved to provide adjusted observation points, as generally illustrated in FIG. 26C, according to the thresholds determined using feedback metric generated from objective measures (e.g. CDP, ECAP, LFP) or subjective measures (e.g. patient-reported paresthesia) for each individual electrode or target pole that was tested (e.g. 8 mm bipole, tripole, multipole). The difference between an expected value of a feedback measure (e.g. ECAP amplitude) and the actual recorded feedback measure can be used to adjust the location of the observational portions that are used to determine the energy allocation to the electrodes. Thus, spinal geometry variations for a real spinal cord environment can be accommodated by changing the spatial observation point coordinates. The inverse algorithm may then be used with the adjusted observation points. A benefit of moving the observation points is improved optimization using a least-squares (overdetermined) function.

Figure 27A:
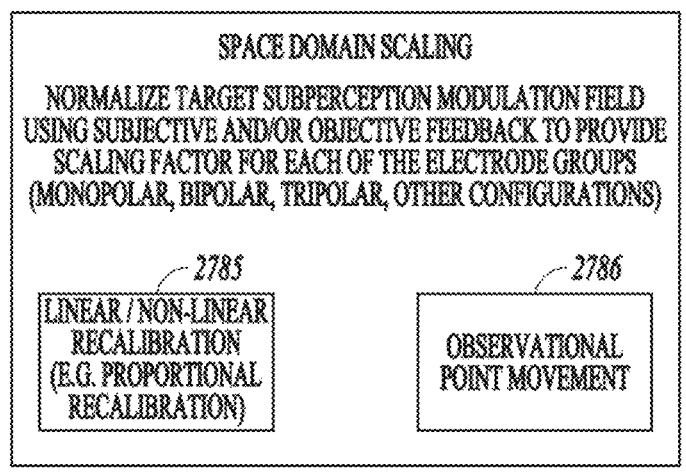
FIGS. 27A-27B generally illustrate, by way of example and not limitation, examples of space domain scaling.
Figure 27B:
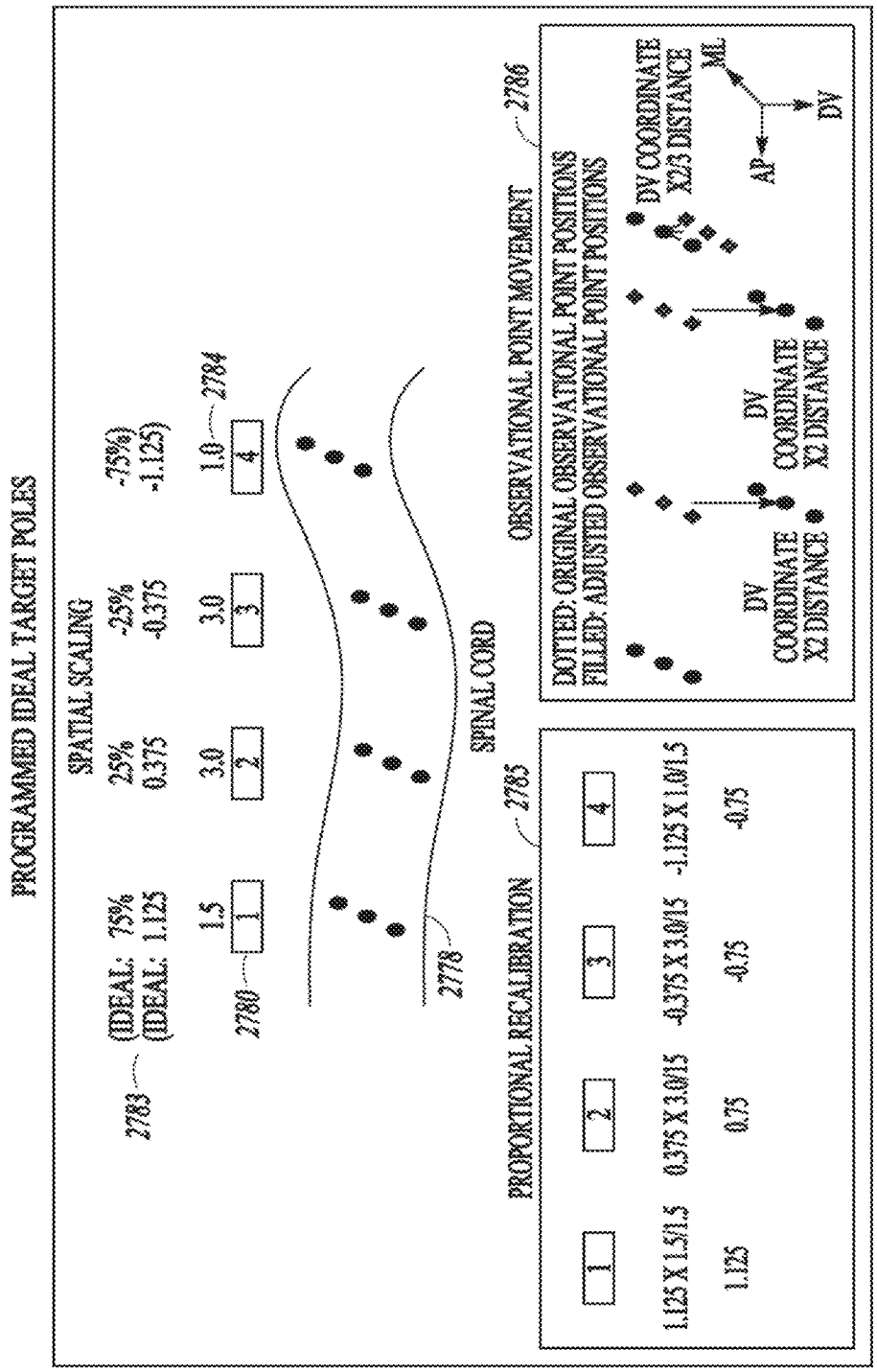

FIGS. 27A-27B generally illustrate, by way of example and not limitation, examples of space domain scaling. The calibration calculation used to normalize the allocated energy may involve simple proportional rebalancing or a more complex inverse modeling scheme. FIG. 27B illustrates a non-uniform spinal cord 2778, and allocated energy values 2783 (e.g. current fractionalizations represented using both percentages and amplitudes) for electrodes 2780 calculated for ideal target poles that assumes uniformity in the spinal cord and uniformity in the alignment between the spinal cord and the electrodes. In the illustrated example, the common total amplitude is 1.5 mA, and the fractionalizations for the ideal target poles are 1.125 mA (or 75%) and 0.375 mA (or 25%) for the anodic constituent sources, and −0.375 mA (or −25%), and −1.125 mA or (−75%) for the cathodic constituent sources. Similar to the previous example, the objective (e.g. biomarker such as CDP, ECAP, LFP threshold) and/or subjective feedback (e.g. patient-reported paresthesia) to the calibration of the electrode groups (one or more electrodes per group) provide a space domain scaling factor 2784 normalizing the field to the real spinal cord environment (e.g. 1.5×, 3.0×, 3.0× and 1.0×).

A linear recalibration process or non-linear recalibration process 2785 may be used to normalize to the greater sum of anodic or cathodic currents. For example, the recalibration process 2785 may be a proportional recalibration process. The baseline for the recalibration process may be a common total amplitude for the ideal currents on the electrodes (e.g. 1.125 mA+0.375 mA=1.5 mA). The calibration may then be the product of the ideal current contribution and the feedback metric for each electrode or electrode group divided by the common total amplitude (1.5 mA). Therefore, in the illustrated the energy contribution of the first electrode is 1.125×1.5/1.5=1.125, the energy contribution of the second electrode is 0.375×3.0/1.5=0.75, the energy contribution of the third electrode is −0.375×3.0/1.5=−0.75, and the energy contribution of the fourth electrode is 0.375×3.0/1.5=0.75.

It is noted that the total anodic current will equal the total cathodic current. Extra cathodic current or extra anodic current may be allocated to the case electrode of the waveform generator. In the illustrated recalibration example 2785, the anodic currents add up to 1.875 mA (1.125+0.75=1.875) and the cathodic currents add up to 1.5 mA (−0.75 mA−0.75 mA=−1.5 mA). As the total anodic currents (1.125 mA+0.75 mA=1.875 mA) is larger than the total cathodic currents (0.75 mA+0.75 mA=1.5 mA), the allocated energy may be normalized to the 1.875 mA value of the total anodic currents. The normalization includes the ideal target energy allocations multiplied by the feedback metric divided by the normalized value. Thus, the contribution of the electrodes may be calculated as follows: 1.125/1.875=60%; 0.75/1.875=40%; −0.75/1.875=−40%; and −0.75/1.875=−40%. The remaining 20% of the anodic current may go onto the case of the implanted pulse generator.

In an observation point movement process to recalibrate, as generally illustrated at 2786, values for the potential $\Phi e$ or electric field E at the spatial observation point are not recalculated. Rather, the distance of the spatial observation points may be moved based on the space domain scaling factors determined from the subject and/or objective feedback. Thus, rather than scaling raw amplitude, the space domain scaling factors 2784 may be used to scale the spatial observation point distances. The baseline for the observation point movement recalibration process may be a common total amplitude for the ideal currents on the electrodes (e.g. 1.125 mA+0.375 mA=1.5 mA). Therefore, the distance between the observation points and the first electrode does not change (1.5/1.5=1), but the distance of the second and third electrodes is doubled (3/1.5=2) and the distance of the fourth electrode is 2/3 (1/1.5=2/3). In some embodiments, the calibration can globally change weighting for the inverse matrix.

Figure 28C:
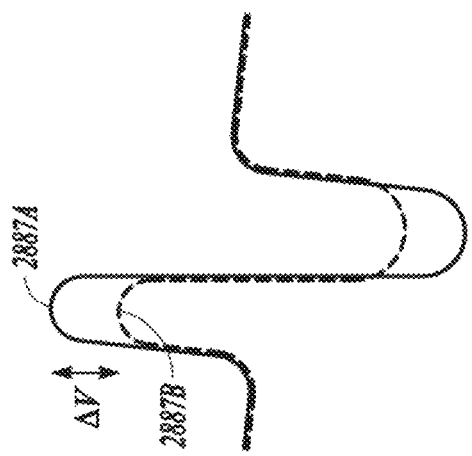
FIGS. 28A-28C generally illustrate, by way of example and not limitation, examples of space domain scaling to compensate for electrode-to-electrode displacement.
Figure 28B:
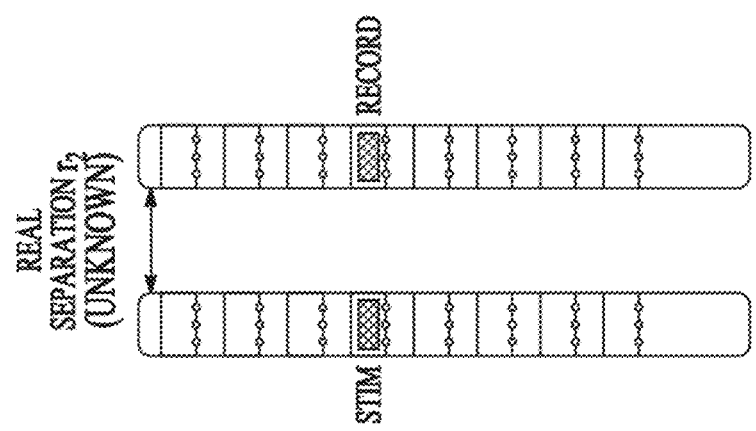
Figure 28A:
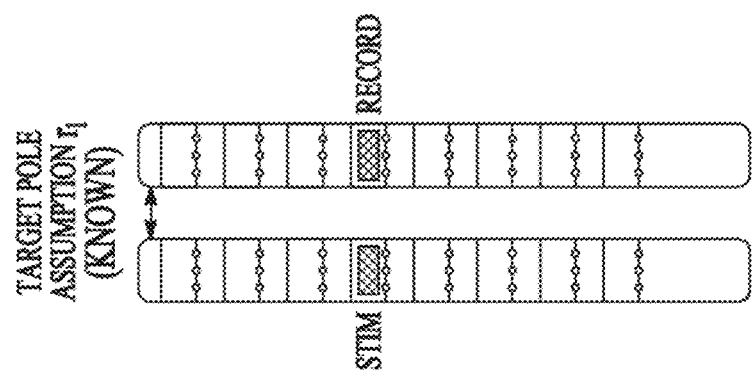

Furthermore, in some embodiments, the spatial observation points may be repositioned based on electrode geometry, rather than or in addition to spinal geometry. FIGS. 28A-28C generally illustrate, by way of example and not limitation, examples of space domain scaling to compensate for electrode-to-electrode displacement. By way of example and not limitation, U.S. Pat. No. 8,380,301, which is incorporated herein by reference in its entirety, discusses determining relative positioning between neurostimulation leads. An electric field may be generated using a first electrode (stimulating electrode) on a lead, and a reference electric parameter may be measured at a reference electrode (recording electrode) on the same lead or as generally illustrated in FIG. 28A, the recording electrode may be on a second lead where the distance between the stimulation and recording electrodes is known. The electric parameter may be measured using second electrode whose distance from the stimulation electrode is not known (e.g. a recording electrode on a second lead whose position is not known). A relationship between the measured electric parameter at the second electrode and at the reference electrode, along with the reference distance, may be used to determine a distance between the first and second electrodes. By way of example and not limitation, the measured electric parameter may be an impedance or a field potential. For example, a change in voltage (a change from the waveform 2887A representing the voltage recorded in FIG. 28A to the waveform 2887B representing the voltage recorded in FIG. 28B) may be used to determine the separation between the recording and stimulation electrodes. Various embodiments of the present subject matter may generate a target pole, and calculate values at observation points before performing the calibration. For example, a point source equation may written as follows: $\Delta V = I\_0/[4\pi\sigma r1] - I0[4\pi\sigma r2]$. The variable r2 may be solved, and the observation point y,z coordinates may be moved by $\Delta r$. Bessel functions, finite element models, can be used or pre-computed for use to calibrate based on $\Delta V$ so long as equations and methods can relate distance from electrode to a change in the obtained signals. Imaging registration/image processing or user-defined electrode separation (e.g. on dragging and dropping lead bodies on a representation of a spinal anatomy) can be used to scale as well. The spatial observation points may be repositioned with the detected position of the electrodes, but the voltage or electric field or activation function values are not recalculated for the repositioned observation points.

Time Domain Scaling

Calibrations may also vary according to the neural element(s) being targeted, especially if multiple field shapes and target poles meant to target distinct neural populations are placed. Various embodiments may scale the allocated energy (e.g. electrode fractionalizations/amplitudes) to provide the sub-perception field according to the electrode-to-electrode relative thresholds and a specific, user-defined neural target.

The threshold current required to stimulate excitable tissue has a relationship to a pulse duration, where shorter pulse widths require larger current amplitudes to stimulate the excitable tissue, and longer pulse widths require smaller current amplitudes to stimulate the excitable tissue. This relationship between pulse widths and stimulation threshold (amplitude) may be plotted as a strength duration curve. However, strength duration concepts are not limited to pulsed stimulation, as these concepts may also be applied to different waveform shapes. Strength-duration relationships may also differ by waveform shape, and separate strength-duration equations may be fit/saved for each waveform type (e.g. passive recharge vs. biphasic active recharge vs. sinusoidal). Strength-duration curves from different waveforms may be displayed at the same time and compared, as shown, for user reference. A user may be presented with strength-duration curve corresponding to neural element being targeted that may adapt after user changes settings. For example, when a neural element and a waveform are selected at same time, then multipliers from neural element effect and waveform effect may be stacked by multiplying the neural element factor with the waveform factor, and applying the resulting product to the original target pole configuration. Strength-duration relationships may also differ by waveform shape, and separate strength-duration equations may be fit/saved for each waveform type (e.g. passive recharge vs. biphasic active recharge vs. sinusoidal). Visually, strength duration curves for different neural element targets may differ. Strength duration curve may be displayed as current/voltage vs. pulse width or normalized threshold vs. pulse width.

Figure 29:
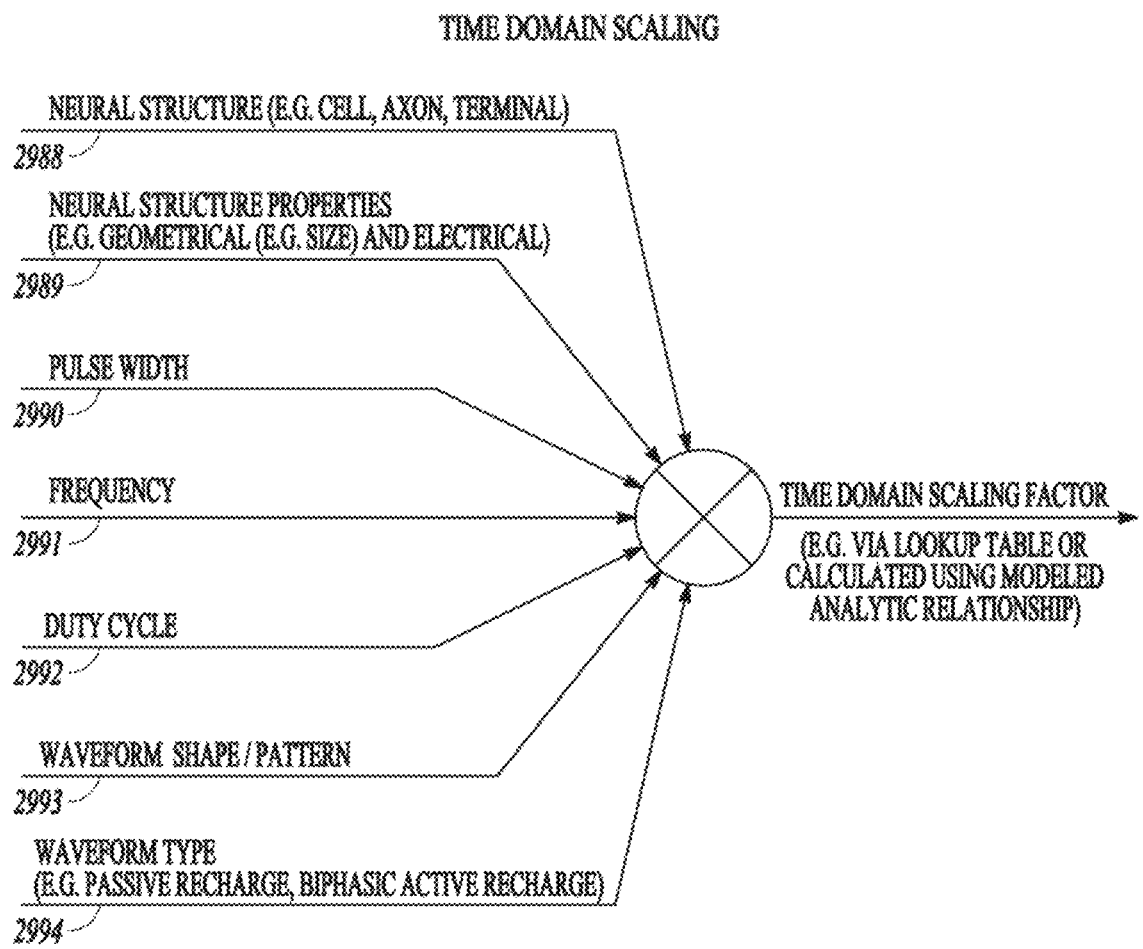
FIG. 29 illustrates some examples of contributing time domain scaling factors that may be stacked or multiplied together to provide an overall time domain scaling factor that may be used to normalize a target sub-perception field.

FIG. 29 illustrates some examples of contributing time domain scaling factors that may be stacked or multiplied together to provide an overall time domain scaling factor that may be used to normalize a target sub-perception field in a manner that may account for neural structure, size, pulse widths, frequencies, waveform shapes and/or waveform types to provide a scaling factor for each electrode group (monopolar, bipolar, tripolar, or other multipolar arrangement). For example, scaling factors (i.e. by how much a given threshold and total electrode fractionalization is scaled by) may vary by various neuron-related and waveform-related variables, including but not limited to structure type (e.g. cell, axon, terminal) 2988, neural structure property 2989 such as a geometrical property (e.g. size such as a nerve diameter) or an electrical property, waveform pulse width 2990, rate 2991, duty cycle 2992, waveform shape or pattern 2993, and waveform such as a passive recharge or biphasic active recharge 2994. Some scaling factors will be pre-determined off-line (e.g. waveform effects, fiber diameter effects), and others may vary according to an internal lookup table or may be calculated internally using an analytical equation that relates threshold to parameter (e.g. strength-duration curve threshold multipliers, rate multipliers). An overall time domain scaling factor, based on one or more of the contributing time domain scaling factors may be determined via a lookup table or calculated based on a model.

In a non-exclusive embodiment, strength-duration relationships (Weiss, Lapicque, or otherwise) derived from offline simulations and/or on-board biophysical simulators may be saved on the device as a lookup table. That is, simulation apriori may be used to derive a scaling factor. The stored lookup table may be used to scale individual thresholds at different electrodes to maintain target pole effects across different neural elements. The lookup table may be specific to a specific combination of a waveform and target. In some embodiments, a built-in graphical user interface (GUI) function may be designed to enable a user to specify different neural targets at distinct electrodes and electrode groups.

Figure 30:
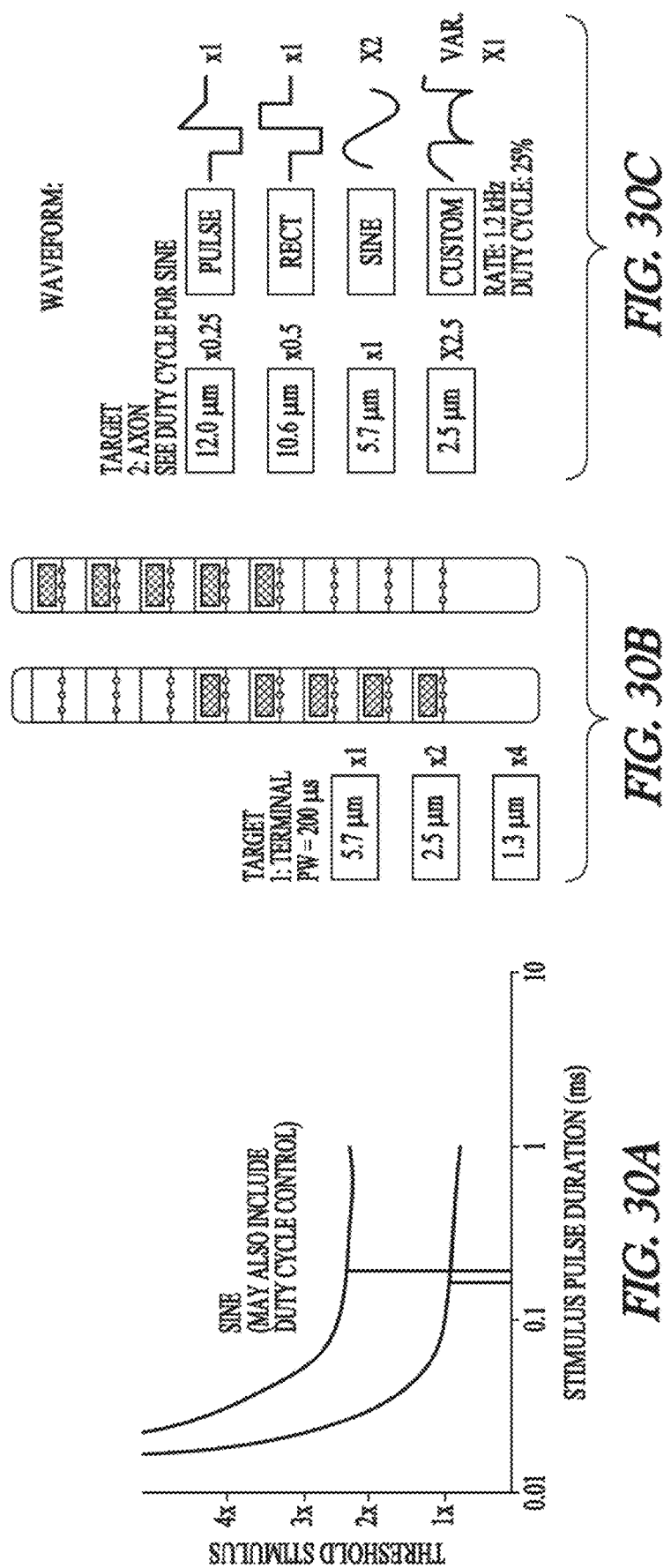
FIGS. 30A-30C provide an example of time domain scaling factors.

FIGS. 30A-30C provide an example of time domain scaling factors. In the illustrated example, two leads that uses two timing channels to target two areas (e.g. Target 1 and Target 2). FIG. 30A illustrates the different strength duration curves for a pulse waveform and sinusoidal waveform which generally illustrates a time domain scaling factor for the different waveforms based on the effectiveness of these waveforms to excite the neural tissue. The system may receive selections from the user through the GUI to identify a neural target by nerve size in µm or by type (e.g. terminal, dorsal column (DC) axon, dorsal root (DR) axon, or nerve cell). Each of these selections may be associated with a time domain scaling factor that also provides an indication of the excitability of those neural targets.

In some embodiments, an algorithm may automatically specify different targets depending on the waveform being delivered. By way of example and not limitation, a 50 Hz signal may default to dorsal columns, and a high rate stimulation may default to terminals. Various embodiments of the system may display scaling factors to the user and/or strength-duration curves at a given frequency.

For example the pulse width for the first lead (Target 1) is illustrated 200 µs and the pulse width for the second lead (Target 2) is illustrated as 90 µs and a frequency of 1.2 kHz. A different multiplication may be applied for the first lead depending on the nerve size of terminals. In the illustrated non-limiting example, a nerve size of 5.7 µm may have a factor of 1, a nerve size of 2.5 may have a factor of 2, and a nerve size of 1.3 µm may have a factor of 4. Similarly, a different multiplication may be applied for the second lead depending on the neural target, such as but not limited to terminal, dorsal column (DC) axon, dorsal root (DR) axon, or nerve cell, and waveform. Examples of waveform may include, but are not limited to pulse, rectangular, sinusoidal, or custom.

Figure 31:
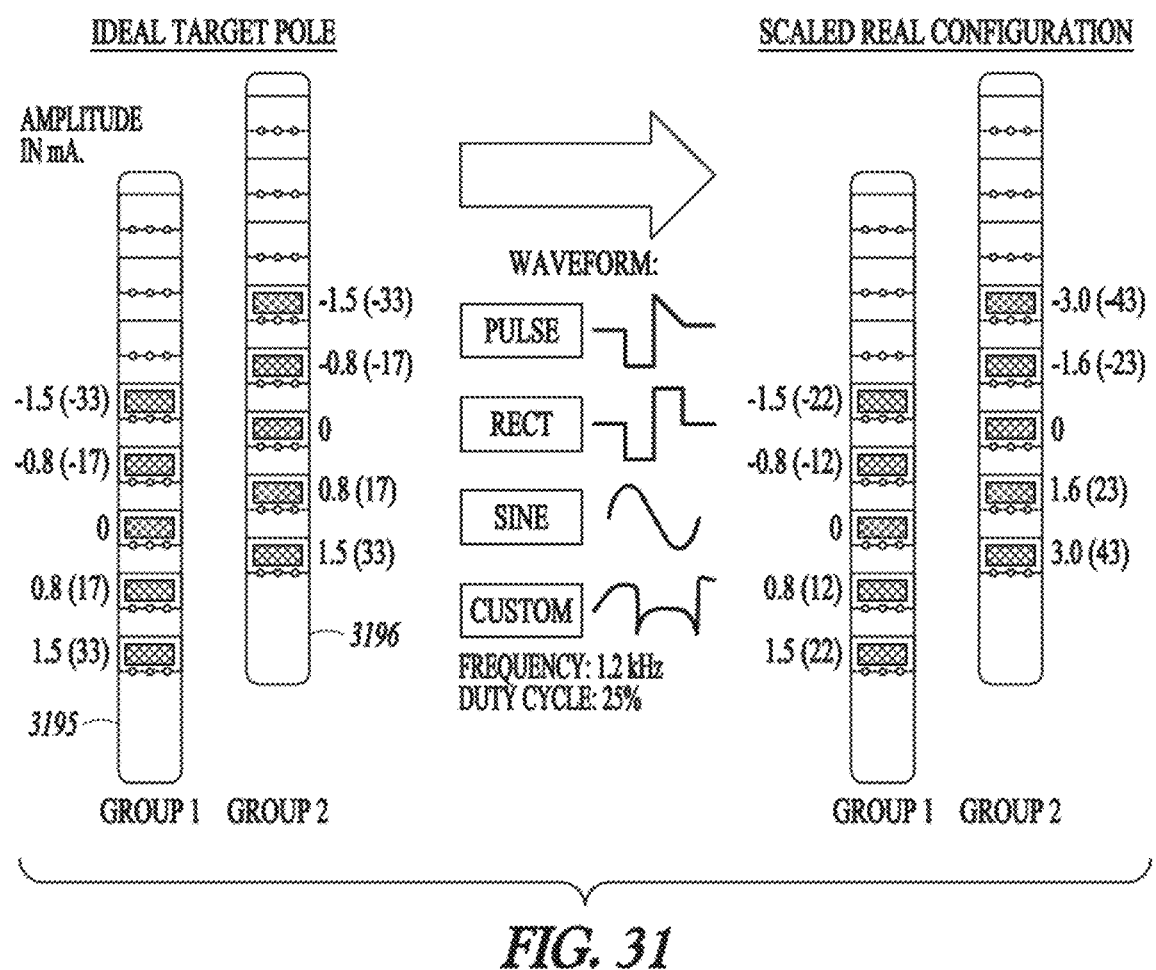
FIG. 31 illustrates a non-limiting example for using time domain targeting.

Space domain factors may be used to first to calculate electrode amplitudes/configurations based on electrode and spinal geometry as previously described, and then time domain targeting may be used to scale the total current delivered through an electrode or group of electrodes corresponding to specific waveform neural target according to values of the applicable strength duration curve. FIG. 31 illustrates a non-limiting example for using time domain targeting. A target pole may be programmed using two leads 3195 and 3196 which may be staggered leads as illustrated. The anodic current and the cathodic current are split equally in the illustrated, such that each lead has 50% of the anodic current and 50% of the cathodic current. More particularly, the anodic contribution of each lead may use a first anodic electrode and a second anodic electrode, and the cathodic contribution of each lead may use a first cathodic electrode and a second cathodic electrode. Even more particularly, the illustrated example indicates that the first anodic electrode for each lead contributes 17% of the anodic current, the second anodic electrode for each lead contributes 33% of the anodic current, the first cathodic electrode for each lead contributes 17% of the cathodic current, and the second cathodic electrode for each lead contributes 33% of the cathodic current. The amplitude of the current contributions may be 0.8 mA for the first anodic electrode for each lead, 1.5 mA for the second anodic electrode for each lead, −0.8 mA for the first cathodic electrode for each lead, and −1.5 for the second cathodic electrode for each lead. It is noted that the leads may or may not be offset, and that the anodic and cathodic electrode contributions may be balanced or unbalanced on the lead. The waveform delivered using the first group of electrodes (illustrated by way of example and not limitation as being on the first lead 3195) may be a 1.2 kHz pulsed waveform, and the waveform delivered using the second group of electrodes (illustrated by way of example and not limitation as being on the first lead 3195) may be a 1.2 kHz sinusoidal wave with a 25% duty cycle. Based on an apriori simulation or based on a modeled analytic relationship of the waveform to threshold of the neural target, it may be determined that the neural target for the second group of electrodes has a strength duration threshold for the sinusoidal waveform has a relationship to the strength-duration threshold of the first group of electrodes for the pulsed waveform. In the simplified example illustrated in FIG. 31, the relationship is that the neural target for the second group of electrodes has a strength duration threshold for the sinusoidal waveform is twice the strength-duration threshold of the first group of electrodes for the pulsed waveform. Thus, the multiplication factor for the time domain targeting is 1× of the amplitude of the current contribution for the first group of electrodes and 2× of the amplitude of the current contribution for the second group of electrodes. The ratio of the current contributions for the first and second leads changes from 1:1 for the ideal target pole to 1:2 for the scaled real configuration. The amplitude of the current contributions for the first group of electrodes remains the same: 0.8 mA for the first anodic electrode, 1.5 mA for the second anodic electrode, −0.8 mA for the first cathodic electrode, and −1.5 for the second cathodic electrode. However, the amplitude of the current contributions for the first group of electrodes is doubled: 1.6 mA for the first anodic electrode, 3.0 mA for the second anodic electrode, −1.6 mA for the first cathodic electrode, and −3.0 for the second cathodic electrode. Fractionalizations are adjusted according to scaled current/total current. The total of the fractionalizations add up to 100%. In the illustrated embodiments, the percentages do not include decimals, so rounding may cause the fractionalized percentage of the second lead to be slightly different from twice the percentage of the first lead. Given the 1:2 ratio of the current contributions for the first and second leads, the first anodic electrode for first lead contributes 12% of the anodic current, the first anodic electrode for second lead contributes 23% of the anodic current, the second anodic electrode for the first lead contributes 22% of the anodic current, the second anodic electrode for the second lead contributes 43% of the anodic current, the first cathodic electrode for first lead contributes 12% of the cathodic current, the first cathodic electrode for second lead contributes 23% of the cathodic current, the second cathodic electrode for the first lead contributes 22% of the cathodic current, the second cathodic electrode for the second lead contributes 43% of the cathodic current. It is noted that, rather than calculating the current value at each contact and then the fractionalization values using the current values, the programming may be performed by first determining the fractionalization values at each contact, and then the current values using the fractionalization values.

Space Domain and Time Domain Scaling

Various embodiments of the present subject matter allow for both space domain and time domain scaling. Some embodiments enable a user-selected weighting for spatial versus temporal fractionalization adjustments. The weighing may be limited to selection of preprogrammed weight or may be at the discretion of the user. For example, a user interface may include a feature such as a slider or dial used to define transitions between spatial and temporal scaling.

Figure 32:
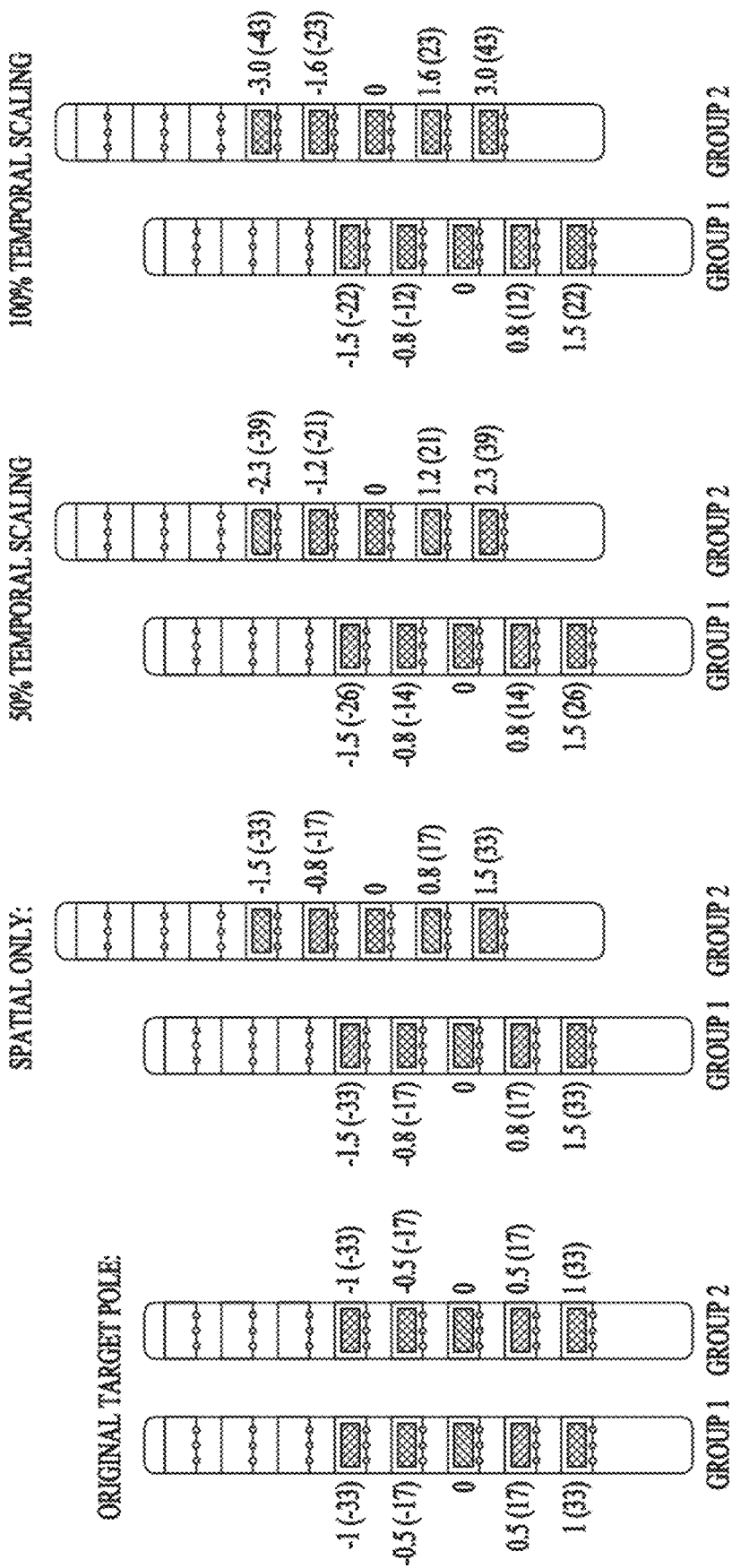
FIGS. 32A-32D illustrate, by way of example and not limitation, scaling allocated energy using both space domain and time domain factors.

In FIG. 32A, the anodic current and the cathodic current are split equally in the illustrated, such that each lead has 50% of the anodic current and 50% of the cathodic current. More particularly, the anodic contribution of each lead may use a first anodic electrode and a second anodic electrode, and the cathodic contribution of each lead may use a first cathodic electrode and a second cathodic electrode. Even more particularly, the illustrated example indicates that the first anodic electrode for each lead contributes 17% of the anodic current, the second anodic electrode for each lead contributes 33% of the anodic current, the first cathodic electrode for each lead contributes 17% of the cathodic current, and the second cathodic electrode for each lead contributes 33% of the cathodic current. The amplitude of the current contributions may be 0.5 mA for the first anodic electrode for each lead, 1 mA for the second anodic electrode for each lead, −0.5 mA for the first cathodic electrode for each lead, and −1 mA for the second cathodic electrode for each lead. It is noted that the leads may or may not be offset, and that the anodic and cathodic electrode contributions may be balanced or unbalanced on the lead.

FIG. 32B illustrates a space domain scaling, which increases the current contribution of each electrode contact by 50%, such that with rounding to the nearest 0.1 mA, the amplitude of the current contributions may be 0.8 mA for the first anodic electrode for each lead, 1.5 mA for the second anodic electrode for each lead, −0.8 mA for the first cathodic electrode for each lead, and −1.5 mA for the second cathodic electrode for each lead. The illustrated space domain scaling is weighted at 100%. It is noted that the space domain scaling could be weighted differently. For example, if weighted at 50%, the increased current contribution at each electrode would only be 25%.

FIG. 32C illustrates 50% time domain scaling at 50%, and FIG. 32D illustrates 100% time domain scaling. The stimulation threshold for the neural target of Group 2 is twice the threshold of the neural target for Group 1. Therefore, for the 50% time domain scaling illustrated in FIG. 32C, the amplitudes of current contribution of each contact may be 150% of the spatial only current contributions. For the 100% time domain scaling illustrated in FIG. 32D, the amplitudes of current contribution of each contact may be 200% of the spatial only current contributions. It is noted that the time domain scaling may be performed first, followed by the space domain scaling.

The transition between spatial and temporal could be linear (as illustrated by the 50% and 100% temporal scaling in FIG. 32C and FIG. 32D), quadratic, or any other monotonic polynomial, exponential, or other relationship. The transitions may also vary according to original target pole (left) rather than and/or in addition to a target pole that accounts for space domain factors.

Figure 33:
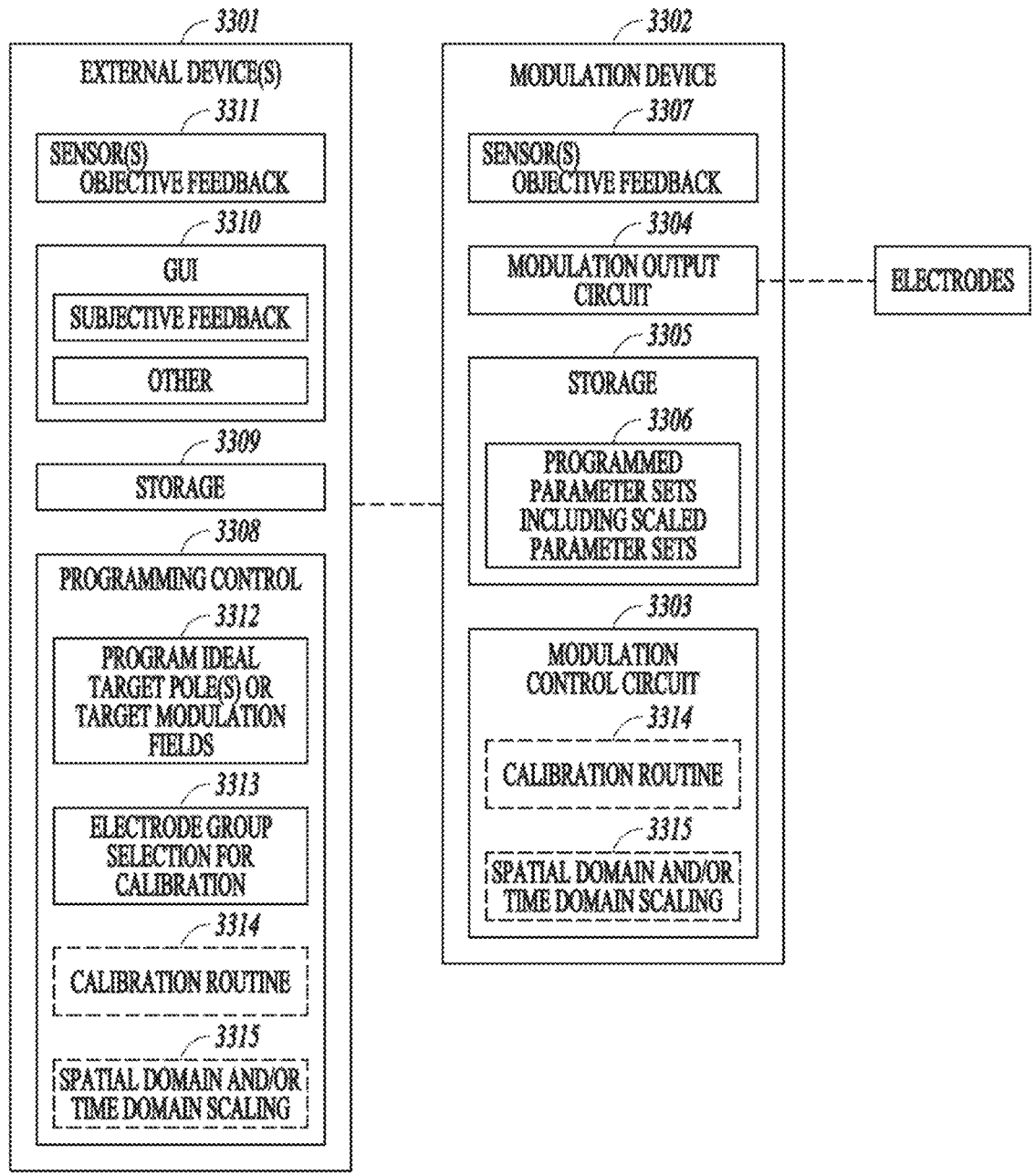
FIG. 33 illustrates an example of a system with components that may be configured to perform various functions discussed herein.

FIG. 33 illustrates an example of a system, with similarities to systems illustrated in FIGS. 2-6, which may include one or more external devices 3301 and at least one modulation device 3302. The system provides additional detail to illustrate components that may be configured to perform various functions described above. The modulation device 3302 may include an external modulation device or an implantable modulation device such as an implantable SCS device. The illustrated modulation device 3302 may include a modulation control circuit 3303 and a modulation output circuit 3304. Storage (e.g. memory) 3305 may include programmed parameter sets 3306, including parameter sets determined using space domain scaling and/or time domain scaling. The modulation control circuitry 3303 may be configured to use the programmed parameter sets to control the modulation output circuit to allocate the energy to the electrodes to provide the desired modulation field. In some embodiments, the modulation device may include sensor circuitry 3307, including or configured to interface with one or more sensors, which may be used to provide an object feedback measure to the neuromodulation. Examples of such measures may include, but are not limited to, ECAPs and LFPs. The external device 3301 may include programming control circuitry 3308, storage 3309, and a user interface 3310 such as a graphical user interface (GUI). The programming control circuitry 3308 may use data and instructions stored in the storage 3309 to program the modulation device 3302 with the parameters sets. Some embodiments, the external device(s) may include sensor circuitry 3311, including one or more sensors, which may be used to provide an object feedback measure to the neuromodulation. Examples of such measures may include, but are not limited to, ECAPs and LFPs. The GUI 3310 may include an interface to receive subjective feedback from the patient, clinician or other user. The GUI 3310 may also include other control and display elements to assist with the programming of the modulation device with the parameter sets.

The illustrated programming control circuitry 3308 includes circuitry 3312 configured to program ideal target pole(s) and/or target modulation fields. Some embodiments may further include circuitry 3313 configured for use in selecting the electrode groups (e.g. monopolar, bipolar, tripolar or other multipolar arrangement) to be used in the calibration process. Calibration routine circuitry 3314, and scaling circuitry 3315 may be incorporated only into the external device(s), only into the modulation device, or distributed between or among the external device(s) and the modulation device. The calibration routine circuitry controls the calibration of the different electrode groups to measure feedback and provide the feedback metric used to scale the allocated energy used to provide the ideal target pole. For example, a calibration routine may be configured to test different combinations if electrodes in a bipole arrangement to provide a feedback metric for each bipole arrangement. The scaling circuitry may be configured to perform functions described above to determine and apply the space domain scaling factor and/or the time domain scaling factor to the allocated energy.

It is noted that a circuit or circuitry may be implemented as part of a microprocessor circuit, which may be a dedicated processor such as a digital signal processor, application specific integrated circuit (ASIC), microprocessor, or other type of processor for processing information including physical activity information. The microprocessor circuit may be a general purpose processor that may receive and execute a set of instructions of performing the functions, methods, or techniques described herein. The circuit or circuitry may be implemented as one or more other circuits or sub-circuits that may, alone or in combination, perform the functions, methods or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified to encode instructions of the specific operation. Instructions may enable embedded hardware (e.g., the execution units or a loading mechanism) to create members of the circuit set in hardware via variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The terms "tangible" and "non-transitory," as used herein, are intended to describe a machine-readable storage medium such as a computer-readable storage medium (or "memory") excluding propagating electromagnetic signals, but are not intended to otherwise limit the type of physical computer-readable storage device that is encompassed by the phrase computer-readable medium or memory. By way of example and not limitation, a machine may include a modulation device or a programming device such as a remote control or clinician programmer. For instance, the terms "non-transitory computer readable medium" or "tangible memory" are intended to encompass types of storage devices that do not necessarily store information permanently, including for example, random access memory (RAM).

The term "machine readable medium" may include a single medium or multiple media (e.g., a centralized or distributed database, and/or associated caches and servers) configured to store instructions, and includes any medium that is capable of storing, encoding, or carrying instructions for execution by the machine and that cause the machine to perform any one or more of the techniques of the present disclosure, or that is capable of storing, encoding or carrying data structures used by or associated with such instructions. Non-limiting machine readable medium examples may include solid-state memories, and optical and magnetic media. In an example, a machine readable medium include: nonvolatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks. Program instructions and data stored on a tangible computer-accessible storage medium in non-transitory form may further be transmitted by transmission media or signals such as electrical, electromagnetic, or digital signals, which may be conveyed via a communication medium such as a network and/or a wireless link.

Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

Various embodiments are illustrated in the figures above. One or more features from one or more of these embodiments may be combined to form other embodiments.

The above detailed description is intended to be illustrative, and not restrictive. The scope of the disclosure should, therefore, be determined with references to the appended claims, along with the full scope of equivalents to which such claims are entitled.

The above detailed description is intended to be illustrative, and not restrictive. The scope of the disclosure should, therefore, be determined with references to the appended claims, along with the full scope of equivalents to which such claims are entitled.

What is claimed is:

1. A method, comprising:
   determining, for at least one target pole, target energy allocations for a plurality of electrodes;
   determining a scaling factor accounting for at least one of: at least one property of a neural target; or at least one property of a neuromodulation waveform; and
   providing a sub-perception modulation field by using the scaling factor to vary the determined target energy allocations for the plurality of electrodes.

2. The method of claim 1, wherein the determining the scaling factor includes determining the scaling factor based on a type of neural structure.

3. The method of claim 1, wherein the determining the scaling factor includes determining the scaling factor based on at least one neural structure property, the at least one neural structure property including a geometrical property or an electrical property.

4. The method of claim 1, wherein the determining the scaling factor includes determining the scaling factor based on a pulse width of the neuromodulation waveform.

5. The method of claim 1, wherein the determining the scaling factor includes determining the scaling factor based on a frequency of the neuromodulation waveform.

6. The method of claim 1, wherein the determining the scaling factor includes determining the scaling factor based on a duty cycle of the neuromodulation waveform.

7. The method of claim 1, wherein the determining the scaling factor includes determining the scaling factor based on a shape or pattern of the neuromodulation waveform.

8. The method of claim 1, wherein the determining the scaling factor includes determining the scaling factor based on a type of the neuromodulation waveform.

9. The method of claim 1, wherein the determining the scaling factor includes determining the scaling factor to account for at least a first property and a second property selected from the group consisting of:
   a type of neural structure;
   at least one neural structure property, the at least one neural structure property including a geometrical property or an electrical property; and
   a neuromodulation waveform property.

10. The method of claim 9, wherein the determining the scaling factor to account for the at least the first property and the second property includes determining a first scaling factor to account for the first property, determining a second scaling factor to account for the second property, and multiplying the first scaling factor and the second scaling factor.

11. The method of claim 1, wherein the determining the scaling factor includes:
    retrieving the scaling factor from a lookup table; or
    calculating the scaling factor from a modeled analytic relationship between a threshold of the neural target and the at least one property of the neural target or of the neuromodulation waveform.

12. A system to program a neuromodulator to deliver neuromodulation to a neural target using a plurality of electrodes, the system comprising a programming control circuit configured to:
    determine, for at least one target pole, target energy allocations for a plurality of electrodes;
    determine a scaling factor accounting for at least one of:
      at least one property of a neural target; or at least one property of a neuromodulation waveform; and
    provide a sub-perception modulation field by using the scaling factor to vary the determined target energy allocations for the plurality of electrodes.

13. The system of claim 12, wherein the programming control circuit is configured to determine a first scaling factor to account for at least a first property and a second scaling factor to account for at least a second property, and multiply the first scaling factor and the second scaling factor, wherein the first and second properties are selected from the group consisting of:
   a type of neural structure;
   at least one neural structure property, the at least one neural structure property including a geometrical property or an electrical property; and
   a neuromodulation waveform property.

14. The system of claim 12, wherein the programming control circuit is configured to retrieve the scaling factor from a lookup table.

15. The system of claim 12, wherein the programming control circuit is configured to calculate the scaling factor from a modeled analytic relationship between a threshold of the neural target and the at least one property of the neural target or of the neuromodulation waveform.

16. A non-transitory machine readable medium containing program instructions for causing a machine to:
   determine, for at least one target pole, target energy allocations for a plurality of electrodes;
   determine a scaling factor accounting for at least one of: at least one property of a neural target; or at least one property of a neuromodulation waveform; and
   provide a sub-perception modulation field by using the scaling factor to vary the determined target energy allocations for the plurality of electrodes.

17. The non-transitory machine readable medium of claim 16, wherein the determining the scaling factor includes determining the scaling factor based on a type of neural structure or based on a geometrical property or an electrical property for a neural structure.

18. The non-transitory machine readable medium of claim 16, wherein the determining the scaling factor includes determining the scaling factor based on a pulse width of the neuromodulation waveform, a frequency of the neuromodulation waveform, or a duty cycle of the neuromodulation waveform.

19. The non-transitory machine readable medium of claim 16, wherein the determining the scaling factor includes determining the scaling factor based on a shape or pattern of the neuromodulation waveform.

20. The non-transitory machine readable medium of claim 16, wherein the determining the scaling factor includes determining the scaling factor based on a type of the neuromodulation waveform.

* * * * *